United States Patent
Srivastava et al.

(10) Patent No.: US 12,409,187 B2
(45) Date of Patent: Sep. 9, 2025

(54) PH REGULATING HYDROGELS THAT NEUTRALIZE CANCER CELL ENVIRONMENT ACIDOSIS AND INCREASE CHEMOTHERAPY EFFICACY

(71) Applicant: Brown University, Providence, RI (US)

(72) Inventors: Vikas Srivastava, East Greenwich, RI (US); Savan Santoki, Rajkot (IN); Zahra Ahmed, Providence, RI (US); Gavin Mays, Sudbury, MA (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 17/710,505

(22) Filed: Mar. 31, 2022

(65) Prior Publication Data

US 2022/0313714 A1    Oct. 6, 2022

Related U.S. Application Data

(60) Provisional application No. 63/168,771, filed on Mar. 31, 2021.

(51) Int. Cl.

| | |
|---|---|
| *A61K 31/704* | (2006.01) |
| *A61K 9/00* | (2006.01) |
| *A61K 9/06* | (2006.01) |
| *A61K 31/136* | (2006.01) |
| *A61K 31/337* | (2006.01) |
| *A61K 31/404* | (2006.01) |
| *A61K 47/02* | (2006.01) |
| *A61K 47/34* | (2017.01) |
| *A61K 47/36* | (2006.01) |
| *A61P 35/00* | (2006.01) |

(52) U.S. Cl.
CPC .......... *A61K 31/704* (2013.01); *A61K 9/0024* (2013.01); *A61K 9/06* (2013.01); *A61K 31/136* (2013.01); *A61K 31/337* (2013.01); *A61K 31/404* (2013.01); *A61K 47/02* (2013.01); *A61K 47/34* (2013.01); *A61K 47/36* (2013.01); *A61P 35/00* (2018.01)

(58) Field of Classification Search
CPC ...... A61K 9/0024; A61K 9/06; A61K 31/704; A61K 31/136; A61K 31/337; A61K 31/404; A61K 47/02; A61K 47/34; A61K 47/36; A61P 35/00
See application file for complete search history.

(56) References Cited

U.S. PATENT DOCUMENTS

| | | |
|---|---|---|
| 8,389,012 B2 | 3/2013 | Palaniappan |
| 9,220,773 B2 | 12/2015 | Chirwa et al. |
| 9,278,077 B2 | 3/2016 | Debrouse |
| 2003/0143274 A1 | 7/2003 | Viegas et al. |
| 2011/0104052 A1* | 5/2011 | Barnett ............... A61K 9/1635 424/1.25 |
| 2018/0185297 A1 | 7/2018 | Debrouse et al. |
| 2019/0321318 A1 | 10/2019 | Dandiker et al. |

FOREIGN PATENT DOCUMENTS

| | | |
|---|---|---|
| CN | 105997538 A | 10/2016 |
| IN | 201941006395 A | 3/2019 |
| WO | 2020076805 A1 | 4/2020 |
| WO | 2020131513 A1 | 6/2020 |

OTHER PUBLICATIONS

Pillai et al., Cancer and Metastasis Reviews, 2019, 38, p. 205-222. (Year: 2019).*
Kumar, D., ed., Cancer Cell Metabolism: A Potential Target for Cancer Therapy, 2020, Springer Nature Singapore Pte Ltd, p. 103-126. (Year: 2020).*
Jin et al., Journal of Controlled Release, 2019, 315, p. 65-75. (Year: 2019).*
Diniz et al., J. Mater. Sci.: Mater. Med., 2015, 26, article 153, 10 pages. (Year: 2015).*
Rizwan et al., Polymers, 2017, 9, article 137, 37 pages. (Year: 2017).*
Ahmed , et al., "Increasing Chemotherapeutic Efficacy Using Doxorubicin and Sodium Bicarbonate Releasing Injectable Chitosan-polyethylene Glycol Hydrogels", bioRxiv, 2023, pp. 1-33.
Brahimi-Horn , et al., "Hypoxia and cancer", Journal of Molecular Medicine, vol. 85, Nov. 2007, pp. 1301-1307.
Brahimi-Horn , et al., "Hypoxia Signalling Controls Metabolic Demand", Current Opinion in Cell Biology, vol. 19, Issue 2, 2007, pp. 223-229.
Cardone , et al., "The Role Of Disturbed pH Dynamics and the Na+/H+ Exchanger in Metastasis", Nature reviews. Cancer, Nov. 2005, pp. 786-795.
Chiche , et al., "Hypoxia-Inducible Carbonic Anhydrase IX and XII Promote Tumor Cell Growth by Counteracting Acidosis through the Regulation of the Intracellular pH", Cancer Research, vol. 69, No. 1, 2009, pp. 358-368.
Chiche , et al., "Tumour Hypoxia Induces a Metabolic Shift Causing Acidosis: A Common Feature in Cancer", Journal of Cellular and Molecular Medicine, vol. 14, No. 4, 2010, pp. 771-794.
Cirillo , et al., "Injectable Hydrogels for Cancer Therapy over the Last Decade", Pharmaceutics, vol. 11, No. 486, Sep. 19, 2019, pp. 1-51.
D'Arrigo , et al., "Gellan Gum Nanohydrogel Containing Anti-Inflammatory and Anti-Cancer Drugs: A Multi-Drug Delivery System for a Combination Therapy in Cancer Treatment", European Journal of Pharmaceutics and Biopharmaceutics, vol. 87, Issue 1, 2013, pp. 208-216.

(Continued)

*Primary Examiner* — Jonathan S Lau
(74) *Attorney, Agent, or Firm* — K&L Gates LLP

(57) ABSTRACT

The invention provides pH regulation systems of buffer-loaded hydrogels that can regulate pH of solutions for long periods of time. These pH-regulating hydrogels may be used in a variety of pH-dependent systems, including water treatment, agricultural soil, and biological applications. Demonstrated is an application in increasing the efficacy of weak base chemotherapeutics used for cancer treatments.

7 Claims, 5 Drawing Sheets

(56) References Cited

OTHER PUBLICATIONS

Gatenby, et al., "A Microenvironmental Model of Carcinogenesis", Nature Reviews, Cancer, vol. 8, Jan. 2008, pp. 56-61.
Gatenby, "Why Do Cancers Have High Aerobic Glycolysis?", Nature Reviews Cancer, vol. 4, 2004, pp. 891-899.
Harguindey, et al., "Proton Transport Inhibitors as Potentially Selective Anticancer Drugs", Anticancer Research, vol. 29 No. 6, 2009, pp. 2127-2136.
Hsu, et al., "Hyaluronic Acid-based Nano-sized Drug Carrier-containing Gellan Gum Microspheres as Potential Multifunctional Embolic Agent", Scientific Reports, vol. 8, No. 731, Jan. 15, 2018, pp. 1-10.
Huber, et al., "Proton Dynamics in Cancer", Journal of Translational Medicine, vol. 8 Article No. 57, 2010, 4 pages.
Kudaibergenov, et al., "Gellan Gum Immobilized Anticancer Drugs and Gold Nanoparticles in Nanomedicine", Academic Journal of Polymer Science, vol. 2, Issue 3, Feb. 2019, pp. 0063-0072.
Lym, et al., "Sulfamethazine-based pH-sensitive Hydrogels with Potential Application for Transcatheter Arterial Chemoembolization Therapy", Acta Biomaterialia, vol. 41, Sep. 1, 2016, pp. 253-263.
Mathers, "Folate Intake and Bowel Cancer Risk", Genes & Nutrition, vol. 4, 2009, pp. 173-178.
Oh, et al., "The Relative Effectiveness of pH Control and Heat Treatment for Enhancing Biohydrogen Gas Production", Environmental Science & Technology, vol. 37, No. 22, 2003, pp. 5186-5190.
Osmalek, et al., "Gellan Gum Macrobeads Loaded with Naproxen: The Impact of Various Naturally Derived Polymers on pH-dependent Behavior", Journal of Biomaterials Applications, vol. 33, Issue 1, Jul. 2018, pp. 140-155.
Palumbo, et al., "Gellan Gum-based Delivery Systems of Therapeutic Agents and Cells", Carbohydrate Polymers,, Feb. 1, 2020, 19 pages.
Parks, et al., "pH Control Mechanisms of Tumor Survival and Growth", Journal of Cellular Physiology, vol. 226, No. 2, Sep. 20, 2010, pp. 299-308.
Pouysségur, et al., "Hypoxia Signalling in Cancer and Approaches to Enforce Tumour Regression", Nature, vol. 141, 2006, pp. 437-443.
Robey, et al., "Bicarbonate Increases Tumor pH and Inhibits Spontaneous Metastases", Cancer Research, vol. 69, Issue 6, Mar. 15, 2009, pp. 2260-2268.
Silva, et al., "The Potential Role of Systemic Buffers in Reducing Intratumoral Extracellular pH and Acid-Mediated Invasion", Cancer Research, vol. 69, Issue 6, Mar. 15, 2009, pp. 2677-2684.
Singh, et al., "In situ Gelling pH- and Temperature-sensitive Biodegradable Block Copolymer Hydrogels for Drug Delivery", Journal of Controlled Release, vol. 193, Nov. 2014, pp. 214-227.
Supuran, "Carbonic Anhydrases: Novel Therapeutic Applications for Inhibitors and Activators", Nature Reviews Drug Discovery, vol. 7, 2008, pp. 168-181.
Swietach, et al., "Regulation of tumor pH and the role of carbonic anhydrase 9", Cancer and Metastasis Reviews, vol. 26, 2007, pp. 299-310.
Tsai, et al., "Preparation and Characterization of Gellan Gum/Glucosamine/Clioquinol Film as Oral Cancer Treatment Patch", Materials Science and Engineering, vol. C 82, 2018, pp. 317-322.
Vicario-de-la-Torre, et al., "The Potential of Stimuli-Responsive Nanogels in Drug and Active Molecule Delivery for Targeted Therapy", Gels, vol. 3, No. 2, E16, May 8, 2017, pp. 1-37.
Wei, et al., "Research Progress in the Application of in situ Hydrogel System in Tumor Treatment", Drug Delivery, vol. 27, No. 1, 2020, pp. 460-468.
Zu, et al., "Cancer Metabolism: Facts, Fantasy, and Fiction", Biochemical and Biophysical Research Communications (BBRC), vol. 313, 2004, pp. 459-465.

* cited by examiner

PH REGULATING HYDROGELS THAT NEUTRALIZE CANCER CELL ENVIRONMENT ACIDOSIS AND INCREASE CHEMOTHERAPY EFFICACY

TECHNICAL FIELD OF THE INVENTION

This invention generally relates to hydrogel compositions, and specifically relates to using hydrogel compositions for regulating pH, neutralizing cancer cell local environment and tumor acidosis, and increasing chemotherapeutic efficacy.

REFERENCE TO RELATED APPLICATIONS

This invention is related to and claims priority under U.S.C. § 119(e) to provisional patent applications U.S. Ser. No. 63/168,771, filed Mar. 31, 2021, the contents of which are incorporated by reference.

BACKGROUND OF THE INVENTION

Acidosis of cancer microenvironments is a well-known characteristic of solid tumors. Microenvironmental acidity of cancer cells produces a selection process of cellular mutations favoring the most aggressive phenotypes. See Rohani et al., Cancer Research 79.8 (April 2019); Tavares-Valente et al., Pharmaceutics 13.2 (February 2021). Cells that continue to proliferate in their acidic environment express increased invasion, metastasis, immune evasion, and chemoresistance. Huber, Seminars in Cancer Biology (2017). One form of chemoresistance is the reduction of cellular chemotherapeutic uptake caused by accumulation of extracellular acids. Ionization of the extracellular space renders weak base chemotherapeutics, e.g., doxorubicin, incapable of permeating through phospholipid cell membranes. This form of chemoresistance is termed "ion trapping". Ion trapping's effects diminish by the neutralization of the tumor microenvironment using bicarbonate buffer delivery in tandem with weak base chemotherapeutics. See FIG. 1. See also. Raghunand, Mahoney, & Gillies, Biochemical Pharmacology, 66.7 (October 2003); Banerjee & Bose, Materials Today Chemistry, 12 (June 2019); Abumanhal-Masarweh et al., Journal of Controlled Release, 296 (April 2018).

Medical scientists have shown that ingestion of bicarbonate as a systemic buffer therapy inhibited the spread of metastasis in cancer mouse models. See Robey et al., Cancer Research, 69.6 (March 2009); Siegler, Midgley, Polman, & Lever, Journal of Strength and Conditioning Research, 24.9 (September 2010). However, oral delivery of bicarbonate in clinical trials was associated with poor patient compliance due to gastrointestinal irritation. Gillies, Pilot, & Mahipal, Journal of Nutrition & Food Sciences. 8.2 (2018). Systemic delivery of pH buffering solutions is impractical as a medical option due to poor bioavailability and non-specific interactions. See Robey et al., Cancer Research, 69.6 (March 2009); Ribeiro et al., Journal of Nutrition & Food Sciences, 01.S2 (2012). Targeted buffering systems enable localized delivery of buffers to maximize therapeutic efficacy while reducing risks of side effects. Previous studies have utilized liposomal and cellulose bicarbonate delivery vehicles to generate short-term pH neutralization. See Abumanhal-Masarweh et al., Journal of Controlled Release, 296 (April 2018) (2019); Chen et al., ACS Applied BioMaterials, 4.4 (April 2021). These studies are limited because they are equivalent to single burst release, lack an active buffering capacity, and thus cannot regulate pH even for a 24-hour timespan.

There is a need in the oncological art for targeted buffering systems that regulate pH of the extracellular cancer environment for a long time to reduce metastasis and increase chemotherapeutic efficacy.

SUMMARY OF THE INVENTION

The invention enables targeted pH buffering by soft material delivery vehicles, such as hydrogel delivery vehicles, to extend the release duration of pH-regulating buffers. The hydrogel encapsulation of buffers described in this specification enables pH regulation through a combination of slow and as-needed rapid buffer release for a weeklong period and possibly more by taking advantage of hydrogel's high loading capacity, uniform distribution of encapsulants, and diffusive slow-release. Hydrogels are polymeric materials characterized by their cross-linked mesh network, hydrophilic nature, high water retention capability, and tunable physical and chemical properties. Hydrogels loaded with drug or pH buffer solutions swell and release encapsulants down concentration gradients between the hydrogel and its environment.

In one aspect, this invention demonstrates the reduction of ion trapping effects using a hydrogel pH-regulating system.

In another aspect, the invention provides an approach to pH-buffer delivery vehicles that can regulate extracellular pH over multi-day intervals.

In a first embodiment, the invention provides hydrogels as delivery vehicles for alkaline or acidic buffer solutions. The inventors demonstrated these hydrogels can prevent ion trapping by buffering acidic cell media. In this embodiment, the delivery vehicles can be from a variety of sizes, including microgels (0.1-500 μm), macrogels (>0.5 mm), or injectable gels are preferred.

The delivery vehicles can be made from a variety of soft materials. Among the useful biocompatible soft materials are gellan, polyethylene glycol (PEG) or PEG derivatives, chitosan, hyaluronic acid, alginate, agarose, polyethylene oxide, polyvinyl alcohol, Matrigel, fibrin, or any combination or formulation of these soft materials.

The delivery vehicles can be loaded with a variety of pH buffer solutions. Among the useful pH buffer solutions, according to the medical requirement, are bicarbonate to reduce acidosis of tumor environments, bicarbonate to reduce diabetic acidosis, bicarbonate to reduce muscle acidosis in muscle fatigue, sodium bicarbonate, calcium bicarbonate, imidazole, lysine and hydroxyl-methyl-amino-methane. Tris, and lactic acid. For other uses, the pH buffer solutions can be sodium hydroxide, hydrochloric acid, sulfuric acid, calcium carbonate, sodium bicarbonate, or magnesium hydroxide. See further Ellis & Morrison, Methods in Enzymology 87.C (January 1982), pp. 405-426; Buffers—A Guide for the Preparation and Use of Buffers in Biological Systems (Calbiochem, 1997); and Perrin & Dempsey, Buffers for pH and Metal Ion Control (Springer Netherlands, April 1979).

In a second embodiment, the inventors used gellan hydrogels and polyethylene glycol diacrylate (PEGDA) hydrogels because of their biocompatibility and favorable tuning of physical properties. See, McAvoy, Jones, & Thakur. Pharmaceutical Research, 35.2 (2018); Choi et al., BioTechniques 66.1 (January 2019); Ferris, Gilmore, Wallace, & in het Panhuis. Soft Matter 9.14 (2013); Coutinho et al., Biomaterials, 31.29 (October 2010). The invention provides and this specification demonstrates the use of pH-regulating PEGDA hydrogels to reverse the effects of ion trapping.

In a third embodiment, the delivery vehicle encapsulates sodium bicarbonate to establish a buffering hydrogel system with the ability to regulate the pH of a solution as required. The inventors tested bicarbonate-loaded PEG hydrogels for their ability to regulate an engineered acidic tumor microenvironment by manipulating its pH level and bringing it closer to the physiological pH of 7.4. The inventors analyzed the effect of sodium bicarbonate on mechanical integrity, swelling kinetics, and cell viability. Bicarbonate increased the porosity in PEG hydrogels, contributing to a lower gel stiffness and higher swelling. The inventors also analyzed bicarbonate-loaded gellan hydrogels for the purpose of regulating the pH of its surrounding solution. These hydrogels were tested for their ability to regulate an engineered acidic tumor microenvironment by manipulating its pH level and bringing it closer to the physiological pH of 7.4. An inverse trend was observed with gellan hydrogels due to possibly enhanced crosslinking caused by $Na^+$ ions.

The inventors investigated the network parameters for swollen hydrogels using modified Flory-Rehner solution theory. The inventors also quantified changes in mechanical integrity, swelling kinetics, and cell viability to investigate the effect of these chemical modifications on the physical properties of the gels.

In a fourth embodiment, the invention provides delivery vehicles for pH regulation in other engineering applications to increase process efficiency or increased desired results. Examples of engineering uses include wastewater treatment, soil pH regulation for agriculture, diabetes, muscle fatigue, renewable hydrogen production.

In a fifth embodiment, the delivery vehicles further include a chemotherapeutic drug. The chemotherapeutic drug can be chosen from the group consisting of doxorubicin, mitoxantrone, sunitinib, paclitaxel, daunorubicin, and other weak base chemotherapeutics (i.e., weak bases like the basicity of doxorubicin). These weak base chemotherapeutics have "ion trapping" behavior and have similar cell uptake improvement with proposed pH reregulating hydrogels. For lists of other weak base chemotherapeutics (including anthracyclines and vinca alkaloids), see Zhitomirsky & Assaraf, Oncotarget, 6(2), 1143-56 (Jan. 20, 2015).

In a sixth embodiment, the buffers and chemotherapy drugs are both loaded into the soft material delivery system for co-delivery. Neutralization of the acidic cancer environment reduces the protonation and sequestering of weak base chemotherapeutics, thus increasing cellular uptake of the chemotherapy drugs.

In a seventh embodiment, the invention provides delivery vehicles for a medical use. The invention provides method of treatment using the delivery system for pH regulation to reduce cancer tumor growth and metastasis by alkalizing the extracellular environment, preventing the emergence of malignant phenotypes in cancer cells. The delivery vehicles can reduce acidosis for reducing cancer metastasis, for reducing cell migration, and for restoring the function of immune cells.

In an eighth embodiment, the invention provides delivery vehicles for actively controlling the pH of a solution to disrupt tumor growth.

In a ninth embodiment, the invention provides delivery vehicles for actively controlling the pH of a solution to retard cancer metastasis.

The inventors tested an invasive breast cancer cell line, MDA-MB-231, for proliferation and percentage viability to assess both the efficacy of bicarbonate treatment and the biocompatibility of PEG hydrogels in vitro. The test results showed how persons having of ordinary skill in the oncological art can develop a simple, effective, and biocompatible therapeutic using bicarbonate modified hydrogels for cancer treatment.

In a tenth embodiment, the invention provides delivery vehicles for actively controlling the pH of a solution to improve chemotherapeutic drug efficacy in cancer treatment. The invention also provides method of treating cancer using hydrogels for pH regulation to improve chemotherapeutic drug efficacy in cancer treatment. Engineered hydrogels may be loaded with pH-regulating buffers and chemotherapy drug or delivered in tandem to chemotherapy drugs to produce similar anti-cancer effects. Using both delivery modalities, hydrogels for pH regulation increase the efficacy of delivered chemotherapy drugs and reduce drug dosage requirements to generate similar anti-cancer effects.

In an eleventh embodiment, the invention provides a method of using the described delivery vehicles, comprising the step of injecting the soft material directly into environments before or after crosslinking using a syringe or similar delivery method.

Gels can be injectable. Gels can be loaded into syringes and photocrosslinked post-injection or, depending on the formulation, they can be thermally crosslinked.

In a twelfth embodiment, the invention provides a method of using the described delivery vehicles, comprising the step of injecting the soft material in a cross-liked form or in a form where the gel forms cross-links in the local environment after being injected.

The invention provides both gellan and PEGDA buffer-eluting hydrogels to regulate the pH of acidic cellular environments through gradual elution of pH buffers. The inventors demonstrate that the gellan and PEGDA buffer-eluting hydrogels can regulate pH in inherently buffered and non-buffered solutions. These hydrogels equilibrate pH to specific values depending on the loaded buffer molecule and magnitude of loading. Periodic addition of bases and acids stimulates increased release of loaded buffers, indicating the hydrogel's regulative ability. These hydrogels neutralize the cancer cell environment from pH 6.8 to pH 7.4, the body's physiologically neutral pH. In vitro investigations further demonstrated that pH neutralization using sodium bicarbonate-eluting PEGDA hydrogels increases the efficacy of weak base chemotherapeutic doxorubicin.

The invention provides gellan and PEGDA hydrogel systems capable of pH-regulation in a variety of solutions, including water, phosphate-buffered saline (PBS), buffered cell culture media, and non-buffered cell culture media. These hydrogel systems can act as adjuvant therapies to promote the cellular uptake of chemotherapeutics.

The inventors developed pH regulating hydrogels using gellan or PEGDA tunable for a wide variety of applications. The inventors can load gels with sodium hydroxide (NaOH), hydrochloric acid (HCl), or bicarbonate ($NaHCO_3$) to maintain a solution's pH against the burst delivery of acidic or alkaline factors. Depending on formulation and loading, these hydrogels modulate solution pH for several days. Mechanical characterization of hydrogels showed that stiffness and swelling ratios change based on the magnitude and type of loading. In vitro studies demonstrated a potential application of base-eluting PEGDA hydrogels. Non-toxic bicarbonate-loaded PEGDA hydrogels rescue consequences of tumor acidosis by diminishing the effects of ion trapping. When delivered in tandem with weak base chemotherapeutics, these base-eluting hydrogels neutralize the extracellular pH of cancer cells and increase doxorubicin efficacy.

Because of the hydrogel's versatility and because of the increasing evidence about the impact of acidosis on immune evasion, the platform for regulating tumor pH can be used to improve the outcomes of other therapies, such as immunotherapy. The inventors used the hydrogels as an adjuvant to the chemotherapeutic doxorubicin, which is commonly used in breast cancer therapy. The inventors characterized and applied the hydrogel formulations as macro-scale biopsy punch-outs. Using suspension polymerization, hydrogel formulations may be applied in microgel formats of 0.1-500 um length scales.

BRIEF DESCRIPTION OF THE DRAWINGS

For illustration, some embodiments of the invention are shown in the drawings described below. Like numerals in the drawings indicate like elements throughout. The invention is not limited to the precise arrangements, dimensions, and instruments shown.

FIG. 2A shows pH regulation using 200 mM $NaHCO_3^-$ loaded into gellan hydrogel formulations. FIG. 2B shows the pH regulation using 400 mM $NaHCO_3^-$ loaded into PEGDA hydrogel formulations. Dashed vertical lines represent instances of external acid addition to the solutions containing hydrogels and the control phosphate-buffered saline solution. In all assays, hydrogels acted to resist acid addition. All values are expressed as mean±standard deviation (n=3).

FIG. 3A show bicarbonate-loaded gellan hydrogels over time in deionized water (DI) adjusted to pH 6.5. FIG. 3B show bicarbonate-loaded PEGDA hydrogels over time in deionized water (DI) adjusted to pH 6.5. FIG. 3C show bicarbonate-loaded gellan hydrogels over time in phosphate-buffered saline adjusted to pH 6.5. FIG. 3D show bicarbonate-loaded PEGDA hydrogels over time in phosphate-buffered saline adjusted to pH 6.5. In deionized water, pH adjustment occurs rapidly and equilibrates over twenty-four hours based on the concentration of loaded bicarbonate. In phosphate-buffered saline, due to the inherent buffering molecules, pH equilibrates gradually over several days. Legend units are mM of encapsulated bicarbonate. Data are shown as mean±standard deviation.

FIG. 4A shows the elastic modulus of gellan gels. FIG. 4B shows the elastic modulus of PEGDA gels. While gellan gels displayed a positive relationship between elastic modulus and concentration of loaded bicarbonate, the inverse is true for PEGDA hydrogels. Each value represents the mean±standard deviation (n=3). The notation * shows p<0.05. The notation  shows p<0.01, and * shows p<0.001 compared with 0 mM sodium bicarbonate and as indicated.

FIG. 5A shows the use of gellan gels. FIG. 5B shows the use of PEGDA gels. Increasing bicarbonate loading reduces swelling ratios in gellan hydrogels, while the inverse is true for PEGDA hydrogels. Each value represents the mean±standard deviation (n=3).

FIG. 6A shows that doxorubicin is significantly more efficacious at preventing cell proliferation at neutral pHs compared to acidic pHs analogous to the tumor microenvironment. FIG. 6B shows that when the proliferation prevented by doxorubicin (grey) is normalized to cell proliferation at each pH value without doxorubicin (total bar height), a concrete trend emerges that demonstrates how the effects of ion trapping weaken as pH rises from 6.4 (the acidic tumor pH) to 7.4 (tissue's neutral physiological pH). Comparing with and without doxorubicin cases at each pH value emphasizes that higher pH values enable doxorubicin to prevent a greater portion of cell proliferation. Proliferation values without doxorubicin (indicated by total bar height) are of *** significance to each other unless otherwise specified* shows p<0.05,  shows p<0.01, and * shows p<0.001. All values are expressed as mean±standard deviation (n=3).

FIG. 7A shows that for MCF-10A healthy breast cells cultured in MEGM, PEGDA was nontoxic up to 600 mM of loaded bicarbonate. FIG. 7B shows that for MDA-MB-231 breast cancer cells cultured in DMEM, PEGDA was nontoxic up to 400 mM of loaded bicarbonate. At high bicarbonate-loading, PEGDA gels induced a pH change above 7.4 which reduced cell viability. All values are expressed as mean±standard deviation (n=3).

FIG. 8A shows doxorubicin is significantly more effective at preventing MDA-MB-231 proliferation when delivered in tandem with PEGDA hydrogels loaded with increasing magnitudes of bicarbonate (mean±standard deviation; n=3). FIG. 8B shows greater bicarbonate loading and pH neutralization enable doxorubicin to prevent a greater portion of cell proliferation (mean±standard deviation; n=2).

FIG. 9A. NaOH-loaded gellan hydrogels can increase the pH of acidic solutions while resisting periodic acid addition. In deionized water (DI) solution, gellan hydrogels loaded with 100 mM NaOH equilibrate pH towards pH 11 within half an hour. This pH regulative ability is preserved despite adding hydrochloric acid (indicated by dashed lines). 100 mM NaOH-loaded gellan hydrogels had an elastic modulus of 108 t 9 kPa. FIG. 9B shows that 13 mM hydrochloric acid-loaded gellan hydrogels demonstrate an ability to adjust the pH of deionized water solution towards an acidic equilibrium despite the periodic addition of bases (indicated by dashed lines). The control group of hydrochloric acid-loaded gellan hydrogels without external base addition decreased from 5.0 to 4.14±0.13 within two hours after adding the hydrogels. Over forty-eight hours, the deionized water solution stabilized to approximately pH 4.0, indicating the equilibrium point of the solution with HCl-loaded hydrogel. With periodic addition of free bases, the solution experienced a slight increase in pH before returning to the approximate pH 4.0 equilibrium. The 13 mM HCl-loaded gellan hydrogels had an elastic modulus of 387 t 38 kPa.

DETAILED DESCRIPTION OF THE INVENTION

Industrial Applicability

Figure 1:
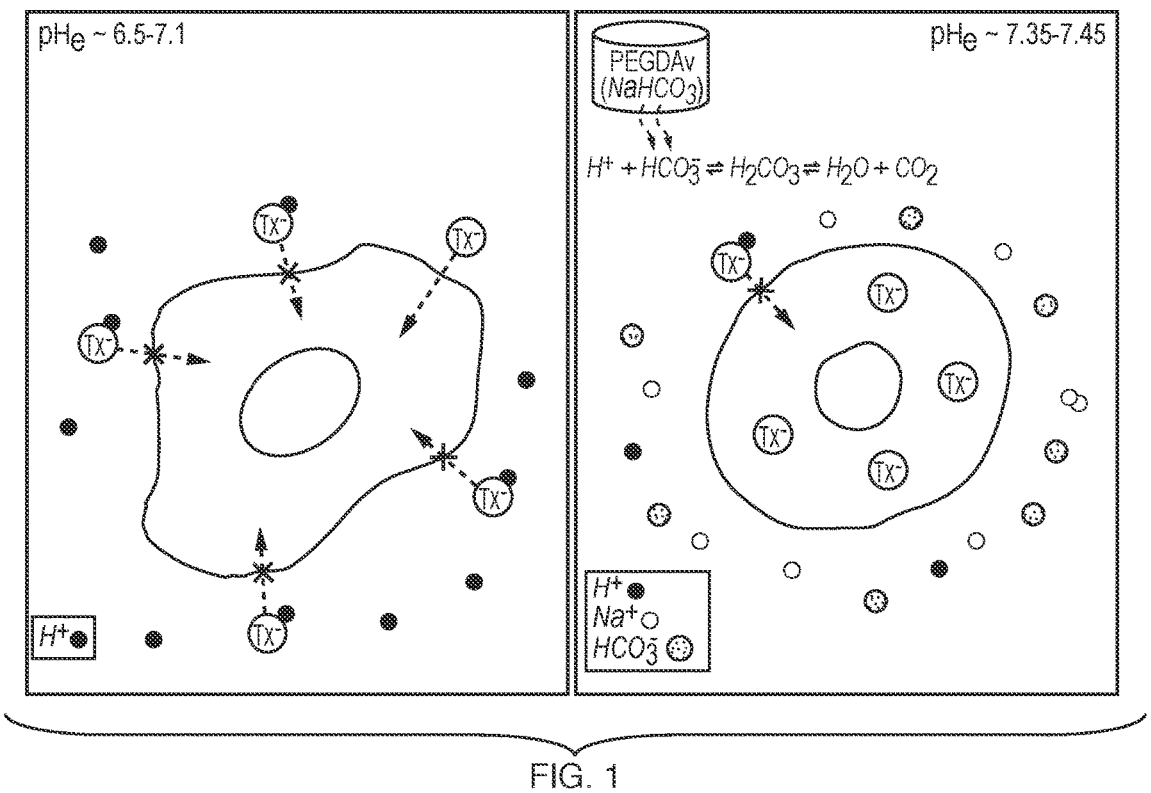
FIG. 1 is a pair of images showing that chemotherapeutic uptake is a defining factor in cancer treatment efficacy. The image on the left side shows weak base chemotherapeutics (Tx−) cannot permeate through lipid bilayers when protonated by extracellular acids in a phenomenon called "ion trapping". In the acidic tumor microenvironment, ion trapping severely hampers chemotherapeutic efficacy. The image on the right side shows gels eluting bicarbonate in the extracellular space can neutralize environmental acidity, removing acids to produce water and carbon dioxide. Neutralization of acids reduces the ion trapping phenomenon and allows for increased weak base chemotherapeutic uptake.

Regulation of pH is crucial for a variety of chemical and biochemical applications. pH governs the effectiveness of many chemical reactions, including bioconjugation reactions that are essential for normal function of the human body. Most biological systems rely on a narrow range of interstitial fluid pH between 7.35 and 7.45 for cell function. See Hopkins, Sanvictores, & Sharma, Physiology, acid base balance. Urolithiasis (September 2021); Michl, Park, and Swietach, Communications Biology 2.1 (December 2019).

Loss of pH homeostasis is severely detrimental to normal bodily function, such as pH induced malignancy in many cancers. The extracellular pH of solid tumors becomes acidified by irregular metabolic pathways, which results in higher expression of metastatic phenotypes and chemotherapeutic resistance. Drug resistance and metastasis are the leading cause of morbidity in cancer. pH neutralization of the tumor microenvironment can increase cellular uptake of weak base chemotherapeutics by reducing the effects of ion trapping.

Definitions

For convenience, the meaning of some terms and phrases used in the specification, examples, and appended claims, are listed below. Unless stated otherwise or implicit from context, these terms and phrases shall have the meanings below. These definitions aid in describing embodiments but are not intended to limit the claimed invention. Unless otherwise defined, all technical and scientific terms have the same meaning as commonly understood by a person having ordinary skill in the art to which this invention belongs. A term's meaning provided in this specification shall prevail if any apparent discrepancy arises between the meaning of a definition provided in this specification and the term's use in the biomedical art.

Acidosis has the oncological art-recognized meaning. Acidosis of cancer microenvironments is a well-known characteristic of solid tumors. See Swietach et al., Philosophical Transactions of the Royal Society B, 369.1638 (March 2014); Damaghi, Wojtkowiak, & Gillies, pH sensing and regulation in cancer (2013). Solid tumor tissues contain an irregular network of blood vessels, causing spatially heterogeneous delivery of nutrients to tumor cells. Loss of uniform oxygen perfusion and increased demand for cell division stimulate cancer metabolism to up-regulate glycolytic pathways. See Pillai et al., Causes, consequences, and therapy of tumors acidosis (June 2019); Luengo et al., Molecular Cell, 81.4 (February 2021), 691-707.e6; Liberti & Locasale, Trends in Biochemical Sciences, 41.3 (March 2016); Fadaka et., Journal of Oncological Sciences, 3.2 (July 2017). Greater diffusion distances between blood vessels and tumor tissue prevents efficient venting of produced lactic acids. The body's inherent bicarbonate pH buffering systems-which interact with acids to produce pH-neutral $CO_2$ and $H_2O$ molecules—are overridden by excessive lactic acid production. Krieg et al., Journal of Pharmaceutical Sciences, 103.11 (November 2014). A consequence of acid accumulation is low extracellular pH ($pH_e \approx 6.5$-$6.8$) which is recognized as a hallmark of cancer progression. Swietach, Cancer and Metastasis Reviews, 38, 1-2 (June 2019).

Administer or administered has the oncological art-recognized meaning of applying, ingesting, inhaling, or injecting, or prescribing an active ingredient (e.g., an acid or base) to treat a host or patient needing treatment. Medically acceptable routes of administration can include the intravenous route, the subcutaneous route, the intraperitoneal route, and the like.

Delivery vehicles, as used in this specification, means a three-dimensional polymer matrix containing selected chemicals released in the environment where this polymer matrix/vehicle is delivered.

Hydrogels, as used in this specification, means a soft three-dimensional polymer matrix that can swell in a solution incorporating the solution and its molecular and ionic contents.

Ion trapping has the oncological art-recognized meaning. One form of chemoresistance is the reduction of cellular chemotherapeutic uptake caused by accumulation of extracellular acids. Ionization of the extracellular space renders weak base chemotherapeutics, e.g., doxorubicin, incapable of permeating through cellular phospholipid membranes. See Raghunand et al., British Journal of Cancer, 80.7 (June 1999); Trebinska-Stryjewska et al., ACS Omega, 5.14 (April 2020).

Liposome or liposomal formulation is a minute spherical sac of phospholipid molecules enclosing a water droplet, primarily as formed artificially, to carry drugs or other substances into the tissues. See, New Oxford American Dictionary, online. A liposome vesicle has at least one lipid bilayer.

Matrigel is the trade name for the solubilized basement membrane matrix secreted by Engelbreth-Holm-Swarm (EHS) mouse sarcoma cells produced by Corning Life Sciences. Matrigel resembles the laminin/collagen IV-rich basement membrane extracellular environment found in many tissues and is used by cell biologists as a substrate (basement membrane matrix) for culturing cells.

Polyethylene glycol diacrylate (PEGDA) is a crosslinker repeating polymer crosslinker and is >80% acrylated. Polyethylene glycol diacrylate (PEGDA, Mw=700 Da) and 1-[4-(2-hydroxyethoxy)-phenyl]-2-hydroxy-2-methyl-1-propanone (Irgacure® 2959) are commercially available from Millipore Sigma. PEGDA 455008-500ML is commercially available from Sigma-Aldrich. PEGDA hydrogels can be fabricated based on protocols adapted from McAvoy, Jones, & Thakur. Pharmaceutical Research, 35.2 (2018). PEGDA hydrogels can be synthesized easily and quickly generating no side products. PEGDA displays compressive modulus ranging from 5-70 kPa. Jabbari et al., PloS one, 10(7), e0132377 (2015). PEGDA can make a PEGDA-only hydrogel in the presence of a free-radical chain photoinitiator and light source. Irgacure-2959. 2-hydroxy-4'-(2-hydroxyethoxy)-2-methylpropiophenone, is a common photocleavable initiator used with PEGDA precursor. PEG-only gels rarely support cell attachment without incorporating cellular attachment sites.

Pharmaceutically acceptable has oncological art-recognized meaning that the formulation does not cause an unacceptable loss of therapeutic activity or intolerable adverse side effects.

Soft materials, as used in this specification, means materials that are easily deformable under forces. Soft materials are polymer matrices with an elastic modulus of less than 10 MPa.

Tris, or tris(hydroxymethyl)aminomethane, known during medical use as tromethamine or THAM, is an organic compound with the formula $(HOCH_2)_3CNH_2$. Tris is extensively used in biochemistry and molecular biology as a component of buffer solutions such as in TAE (Tris base, acetic acid, and EDTA) and TBE (Tris base, boric acid, and EDTA) buffers. Tris (usually known as THAM in this context) is used as alternative to sodium bicarbonate in the treatment of metabolic acidosis.

Unilamellar liposome is a spherical chamber/vesicle, bounded by a single bilayer of an amphiphilic lipid or a mixture of such lipids, containing aqueous solution inside the chamber. Unilamellar liposomes mimic cell membranes and are classified based upon their size.

Unless otherwise defined herein, scientific and technical terms used with this application shall have the meanings commonly understood by persons having ordinary skill in the biomedical art. This invention is not limited to the particular methodology, protocols, and reagents, etc., described herein and as such can vary.

The disclosure described herein does not concern a process for cloning humans, processes for modifying the germ line genetic identity of humans, uses of human embryos for industrial or commercial purposes or processes for modifying the genetic identity of animals which are likely to cause them suffering with no substantial medical benefit to man or animal, and animals resulting from such processes.

Guidance from Materials and Methods

A person having ordinary skill in the oncological art can use these materials and methods as guidance to predictable results when making and using the invention:

Preparation of aellan hydrogels. Polyethylene glycol diacrylate, gellan gum (Gelrite, Mw=1,000,000), calcium chloride, sodium hydroxide, sodium bicarbonate, hydrochloric acid, and phosphate buffered saline (PBS) were purchased from Millipore Sigma. Phosphate-buffered saline tablets are also commercially available from VWR (E404-100TABS). Polystyrene petri dishes were purchased from Fisher Scientific. Glass petri dishes and 8 mm biopsy punches were purchased from VWR. Gellan hydrogels were prepared with sodium bicarbonate loading following methods described in Shukla & Shukla. Journal of Materials Chemistry B, 6 (September 2018); Shukla et al., Journal of Polymer Science, 58.10 (May 2020). Briefly, 500 mg gellan was dissolved in 20 mL MilliQ water at room temperature under constant stirring to obtain a final concentration of 2% w/v. The solution was heated to a temperature of 100° C. until homogeneous. Next, 8.3 mg calcium chloride (Chem-Impex, 99%) and 200 mg sodium hydroxide solution (Sigma, 50%) dissolved in 2.5 mL of MilliQ water was added to the gellan solution. Each were added under constant stirring to a final concentration of 100 mM sodium hydroxide in gellan solution.

Gellan gels with a diameter of 60 mm and height of 10 mm were produced by transferring the solution to a polystyrene petri dish (Fisher) and allowing gelation to occur at 4° C. for approximately one hour. Formulations of gellan gel crosslinkers, encapsulants, and gellation time are shown in TABLE 1. For assays, individual hydrogel samples of 8 mm diameter and 10 mm height were punched out. The same preparation was carried out for indicated concentrations of sodium bicarbonate and hydrogels containing hydrochloric acid (Sigma, 25%). Sodium bicarbonate loading was performed up to a 200 mM $NaHCO_3$ concentration before excessive heating was required for gellation.

TABLE 1

Characteristics of gellan gum (GG) mixtures with different gel agents.

| Gel Agent | pH after mixing | Gelation time |
| --- | --- | --- |
| GG | 5.48 | 3 min |
| GG/1.0 mM NaOH | 7.53 | 3 min |
| GG/50 mM NaOH | 11.94 | 5 min |
| GG/100 mM NaOH | 12.27 | 13 min |
| GG/13 mM HCl | 2.5 | 1 min |
| GG/50 mM $NaHCO_3$ | 8.06 | 2 min |
| GG/100 mM $NaHCO_3$ | 8.40 | 1 min |
| GG/200 mM $NaHCO_3$ | 8.42 | 1 min |

Preparation of PEGDA hydrogels. PEGDA (700) was dissolved in deionized water to produce 10% w/w solutions. Once the PEGDA was fully dissolved/suspended, the desired amount of bicarbonate was then added to the PEGDA (700) solutions and left to dissolve at room temperature. PEGDA hydrogels were prepared with sodium bicarbonate at 0 mM, 50 mM, 100 mM, 200, 400 mM, 600 mM, and 800 mM concentrations. Before photocrosslinking, Irgacure®2959 was dissolved in 70% ethanol in water and stirred into the formulation for a final concentration of 0.5% w/v. In cell culture assays, PEGDA and encapsulated bicarbonate solutions were sterilized by autoclaving. The formulations where then poured into 60 mm diameter glass petri dishes and UV cured. Several 8 mm diameter biopsy punches were taken from each gel for pH assays. An upper limit of 800 mM sodium bicarbonate loading was identified before complete gel formation became compromised.

pH control studies. A Fisherbrand™ Accumet™ AE150 Benchtop pH meter equipped with a ROSS electrode calibrated for low ionic strength solutions was used to measure the pH in all deionized water samples. The pH of phosphate-buffered saline and cell media samples were measured using the Mettler Toledo FiveEasy pH meter and electrode. For pH control assays, sodium hydroxide, hydrochloric acid, and bicarbonate loaded hydrogels were placed in a glass vial containing 15 mL deionized water or 1× phosphate-buffered saline release media adjusted to 10.0, 5.0 and 6.5 for NaOH, HCl and sodium bicarbonate respectively. All the assays were carried out in triplicate. The vials were then stored on a stir plate with gentle magnetic stirring at 20° C. and the pH was measured at predetermined time intervals.

Mechanical assays. The swelling ratio of prepared hydrogels was studied by weighing hydrogel sample punch outs before and after swelling in phosphate-buffered saline (pH 7.4) for seven days at 21° C. The hydrogels at post-swelling equilibrium were blotted to remove excess solution from the surface before weighing. Samples were dried in an oven at 80° C. for twenty-four hours and weighed to obtain the dry weight of the samples for equilibrium water content (EWC) calculation.

Compression testing was performed at room temperature using an MTS Servohydraulic test system machine equipped with a 125 N load sensor and MTS TestSuite software (MTS Systems Corporation, Eden Prairie, MN, USA). Hydrogel samples were prepared polystyrene (for gellan) or glass petri dishes (for PEGDA) with an approximate height of 10 mm and a diameter of 56 mm and stored overnight before compression testing. Mechanical data for each case is presented as an average of three repetitions measured before testing. To prevent slippage of the hydrogel during testing, adhesive was used to increase friction between the hydrogel and the metal plates. The sample was set between compression plates, so the upper plate touched the sample. Compression was performed with a constant 0.0025 sec-1 strain rate, and samples were compressed until 15% strain was reached. The data were analyzed using Matlab. The elastic modulus was calculated from the average linear slope in the elastic region of the stress-strain curve.

In vitro breast cell culture and viability assays. Triple negative breast cancer cell line, MDA-MB-231 (ATCC) was grown in complete Dulbecco's modified Eagle's medium (DMEM+4.5 g/L Gluc+L-Gln-Pyr, Lonza) supplemented with 10% v/v fetal bovine serum (VWR), 1% v/v Penicillin-Streptomycin solution (Caisson Labs). Healthy breast cell line MCF-10A (ATCC) was grown in complete MEGM (MEBM (Lonza)+MEGM SingleQuot Kit (Lonza)) supplemented with 10% v/v fetal bovine serum (VWR), 1% v/v Penicillin-Streptomycin solution (Caisson Labs), and 100 ng/mL cholera toxin (Sigma-Aldrich). Cells were cultured in cell treated polystyrene cell culture flasks (CellStar) at 37° C. in a humidified atmosphere containing 5% CO2.

MDA-MB-231 cells were seeded in 12-well plates (VWR) at a cellular density of 100.000 cells/well and incubated at 37° C. for twenty-four hours in 3 mL DMEM/well to produce adherent monolayers. PEGDA gel components were sterilized by autoclave and the UV curing process. Each PEGDA gel (2 mm thick, 8 mm diameter) was punched out from a glass petri dish, triple-washed in 1× phosphate-buffered saline to remove uncrosslinked PEGDA, and carefully placed into 12-well plate inserts. Well inserts were then placed into wells of adherent cell cultures for media conditioning. Well plates were incubated for an additional five days after gel exposure. After incubation, the top 2 mL of media was removed for pH measurements. Gentle aspiration was performed to remove PEGDA gels from the wells and the viability of remaining cells was quantified using MTT assays and cell counting. MTT assays were performed using protocols and MTT kit purchased from Oz Biosciences. MTT working solution was introduced to the cells after a gentle phosphate-buffered saline wash and MTT crystals were allowed to form for four hours.

After MTT crystallization, working solution was aspirated and a DMSO solubilization solution was used to dissolve crystals. Using a spectrophotometer, optical density (OD) at 570 nm and a reference 650 nm were measured and cell viability was calculated as the noise-corrected OD ($OD_{570}$-$OD_{650}$) for each sample normalized to the noise-corrected OD of the control case. Viability trends were confirmed using manual cell counts. Manual cell counting was performed using a cell suspension of 50% trypan blue on a hemacytometer. Cell viability for each case was calculated as the number of living cells divided by the total live and dead cells.

Statistical analysis (1). Statistical analysis was performed using the Statistics Toolbox in Matlab. Data are represented as mean±standard deviation. Single comparisons were made using an unpaired t-test. One way analysis of variance (ANOVA) followed by Tukey's HSD post hoc test was used for data sets with multiple comparisons. A value of $p<0.05$ was considered a statistically significant difference.

Statistical analysis (2). For the swelling and mechanical testing data, statistical analysis was performed using one-way and two-way ANOVA followed by Tukey's multiple comparisons using GraphPad Prism Version 9.1.0 (216) formacOS.

The data was reported as mean and standard error of mean (n:2'. 3), and the statistical differences between control (no bicarbonate) and the treatment groups (gels with bicarbonate) were reported with the obtained p-values. Statistically significant effect of the treatment group was considered for $p<0.05$.

Construction of hydrogels. Hydrogels or hydrophilic gels are polymeric materials characterized by cross-linked network mesh structure displaying extensive water retention capabilities. The polymeric backbone formed by natural or synthetic monomers attracts water molecules, while the crosslinked network prevents chain degradation. This uptake is a consequence of complex polymer-solvent interaction, which considers the thermodynamics behavior of polymer solutions and is quantitatively described using Flory-Huggins interaction parameter, X, described in the Flory-Huggins theory. See Ganji, Vasheghani, & Vasheghani, Theoretical description of hydrogel swelling: A review (2010).

Because of their reversible swelling and des welling behavior, desirable viscoelastic and mechanical properties, high porosity, high absorption capacity, tunable cross-linking and mesh size, and a range of stimuli to respond in specific environment, hydrogels have become useful in the biomedical industry for a range of applications. Hydrogels loaded with drug cargo, designed to respond to a specific stimulus, rapidly deswell and release the cargo when and where desired. A range of physical (temperature, electric and magnetic fields, pressure) and chemical (pH, molecular targets, ionic strength) stimuli have presented themselves as useful cues to control hydrogel behavior. See Ganji, Vasheghani, & Vasheghani, Theoretical description of hydrogel swelling: A review (2010).

Hydrophilic gels for biological uses were first identified in the 1960s, where the properties such as the ability to hold water content and permeability for metabolites in the body along with biocompatibility allowed them for drug delivery. Calo & Khutoryanskiy, Biomedical applications of hydrogels: A review of patents and commercial products. European Polymer Journal, 65, 252-267 (2015). Combined with their ability to hold hydrophilic drugs along with high water content, and reduction of drug denaturation pushed them at the frontier of drug delivery. Li & Mooney, Nature Reviews Materials, 1 (12), 1-17 (2016). Hydrogels in the macroscopic size range can capture drugs ranging from small molecules to biologics in their porous structure, where there are interactions between the polymer chains and the encapsulated drugs on micro and nanoscales. Besides drug delivery, hydrogel have been used as tissue-engineering scaffolds, biosensors, and self-healing materials extensively. Chai, Jiao, & Yu, Gels, 3(1), 6 (2017).

To accurately tune the behavior of hydrogels, a control of its network structure is required. Hydrogel network is characterized by polymer backbones, which are connected via physical or chemical crosslinks forming a network mesh represented by a mesh size. The mass swelling ratio ($Q_m$) and volume swelling ratio ($Q_v$) define the equilibrium swelling a hydrogel undergoes in a solvent. Polymer volume fraction in the swollen state (02, s) and the average molecular weight between two crosslinks (Mc) are crucial in determining the properties of a hydrogel. Zhu &. Marchant, Design properties of hydrogel tissue-engineering scaffolds. Expert review of medical devices, 8(5), 607-626 (2011).

Hydrogels can be prepared from natural or synthetic polymers. The optimal design of a hydrogel is a balance between its stiffness and elasticity, to allow it to deliver cargo m the body without undergoing degradation.

The choice of material is important, remembering the hydrogels must not be cytotoxic or elicit an immune response. Biologically derived hydrogels are frequently chosen for their biocompatibility. Examples of natural polymers to form hydrogels include various polysaccharides such as hyaluronic acid, starch, chitosan, alginate, cellulose, collagen, gellan gum, agarose, and gelatin. Synthetic polymers overcome weak strength and can be combined with natural monomers to form mixed hydrogels. Synthetic polymers are advantageous for their consistent formulations—lending to their ease of reproducibility—and tenability. Examples of synthetic hydrogels include those derived from vinyl and acrylic monomers like ethylene oxide, methacrylic acid, etc., and polyethylene glycol derivatives. See Nikolic, Zdrnvkovic, Nikolic, & Ilic-Stojanovic, Synthetic hydrogels and their impact on health and environment. Cellulose-Based Superabsorbent Hydrogels, 1-29 (2018).

Methods of synthesis for hydrogels can vary widely depending on the monomer type, the chemistry of polymer and the crosslinker, and the mechanical properties desired. There can be two crosslinking types—physical and chemical, where the physical crosslinking is inherently weaker than chemical. Physical crosslinking can be achieved via crystallization, ionic interaction, or hydrogen bonding, whereas chemical crosslinking involves reaction between functional group on the polymer chain with the crosslinking agent. Several polymerization techniques can form hydrogels including solution and suspension polymerization.

Stimuli responsive hydrogels provide an opportunity for drug delivery at exact stimulus that can be controlled depending on where the drug cargo needs to be unloaded. Hydrogels that respond to a pH stimulus to unload the therapeutic agent are called pH responsive hydrogels. Such hydrogels include a "pendant group" that ionizes and generates electrostatic interaction responsible for swelling and deswelling of the gels. Gupta, Vermani, & Garg, Drug Discovery Today, 7(10), 569-579 (2002). Anionic hydrogels swell at a pH above the polymer pK, where cationic hydrogels swell at a lower pH. Such a response to a pH stimulus is controlled by the charge on the polymer, the pK, and the crosslinking density of the gel network.

Manipulation of localized acidity via hydrogels. Regulating pH within the body is of prime importance for normal functioning. An acid-base homeostasis is maintained in the body primarily via a bicarbonate $HCO_3/CO_2$ buffer regulated by kidneys This steady state maintenance of the systemic pH can be disrupted under extreme circumstances. Lactic acidosis can be induced because of excessive lactic acid production by the cells, which can lower the pH from the normal levels of 7.35-7.45. A lactic acid production of greater than 2 mmol/L induces extracellular acidity that can be potentially fatal. Cohen, Woods, & Krebs, Clinical and biochemical aspects of lactic acidosis, Vol. 162. (Oxford; Blackwell Scientific Publications: 1976). A common cause of excessive lactic acid production is strenuous exercising that can lead to a mismatch between the oxygen demand and supply, giving rise to lactate production in the muscles leading to contractions.

A rather localized case of lactic acidosis happens at the cancer tumor site. Cancer cells do not undergo aerobic glycolysis that is the metabolic pathway used by normal cells to produce energy. Under normal circumstances, most cells metabolize glucose to carbon dioxide by the oxidation of pyruvate to produce large quantities of Adenosine Triphosphate (ATP) and less lactate, via a process called Oxidative Phosphorylation or OXPHOS. When the aerobic conditions are absent, cells produce large quantities of lactate, and less ATP. Luengo et al., Molecular Cell. 81(4), 691-707 (2021).

Cancer cells undertake the anaerobic pathway of metabolizing glucose even in the presence of oxygen, a phenomenon first observed by Otto Warburg. The cause of Warburg effect is a heavily researched topic in oncology. Latest advances in the field suggest that when the demand for nicotinamide adenine dinucleotide ($NAD^+$) enzyme exceeds that of ATP, the cells engage in anaerobic glycolysis despite the presence of oxygen.

The important consequence of Warburg effect is that it changes the ratio of extracellular $pH_e$ and intracellular $pH_i$ of the cancer cells, giving rise to a localized acidic extracellular environment around the tumor site. Manipulation of this skewed $pH_e/pH_i$ ratio has been used to develop cancer therapeutics for cancer cells with more aggressive phenotypes. Hao, Xu, & Li (2018). RSC Advances, 8(39), 22182-22192. Modification of acidity around tumors has been shown to reduce cancer aggression, by affecting angiogenesis and invasiveness. Robey et al., Cancer Research, 69(6), 2260-2268 (2009).

pH responsive hydrogels have been employed to address this acidification observed in tumor microenvironment (TME). Chitosan-grafted-dihydrocaffeic acid pH responsive hydrogels have been examined for their pH sensitive swelling and release of anticancer drug Doxorubicin. Liang et al., Journal of Colloid and Interface Science, 536, 224-234 (2019). Such stimuli responsive smart hydrogels are becoming increasingly common due to their excellent efficacy and localized delivery of drugs at the cancer sites.

While the acidity of tumor microenvironment can trigger release of drugs from pH stimulated hydrogels, another domain of interest has been a direct manipulation of this acidity by direct neutralization using a basic reagent, or inhibition of proton pumps on the cancer cells. Aggressive breast cancer cell line MDA-MB-231 displayed minimized incidence of metastases when the $pH_e$ of the tumor was neutralized by a direct dose of bicarbonate. McCarty & Whitaker, Altern. Med Rev, 15(3), 264-72 (2010). in a rodent model. While patients can take bicarbonate orally, the higher dosage to counter the acid load from the tumor might cause misbalanced physiological levels of bicarbonate, resulting in adverse side effects. Another study effecting the use of sodium bicarbonate in liposomal drug carrier system as an adjuvant showed a 21-fold increase in the drug uptake in a triple negative breast cancer cell line. Robey et al., Cancer Research, 69(6), 2260-2268 (2009).

Bicarbonate has been studied as an adjuvant in chemotherapy or as an ad-libitum therapeutic, but not solely as a drug for localized delivery without as an adjuvant. The promise of biocompatible hydrogel systems for producing such an effect is high.

Gellan gum hydrogels. Gellan gum is an anionic polysaccharide with repeating units of glucose, glucuronic acid, and rhamnose.

When a heated aqueous solution of gellan gum is cooled down, the polymer chains undergo conformational transformation giving rise to a double helical structure via coil to helix transformation. Matricardi et al., Molecules, 14(9), 3376-3391 (2009).

Chain-chain repulsions are present in virgin polymeric structure due to the negatively charged glucuronic acid, resulting in weak gels. Addition of cationic salts results in the formation of crosslinked structure, with greater positive charge leading to higher strength of crosslinking.

High concentration of salts results in chain aggregations leading to weaker gels. Norris, Nishinari, & Rinaudo, Food Hydrocolloids, 28(2), 373-411 (2012). Polyelectrolytic and ionic crosslinking via alginate and other cations provide an effective synthesis route for gellan gum, however this strength might be compromised in the physiological conditions where a swapping of the cations of a lower valence from the blood plasma might cause faster degradation. Methacrylation and formation of interpenetrating polymer network (IPN) might be adopted to enhance the gel stiffness.

Polyethylene glycol (PEG) hydrogels. Polyethylene glycol has been studied in the field of drug delivery due to its high biocompatibility, versatile chemistry, and non-fouling behavior in vivo. Functionalized PEG monomers containing reactive chain ends can be covalently crosslinked via chain or step growth mechanisms to provide stable gel structures Zalipsky & Harris, Introduction to chemistry and biological applications of polyethylene glycol (1997). Most commonly. PEG diacrylate and dimethacrylate are used in drug delivery applications for their polymerization properties that enable ease of drug encapsulation. While chain growth photopolymerization is widely preferred, PEG hydrogels developed via step-growth 'click' chemistry have displayed the added benefit of providing bioconjugation as well as excellent mechanical stability. Kolb, Finn, & Sharpless, Angewandte Chemie International Edition, 40(11), 2004-2021 (2001).

Photocrosslinking is an easy and efficient way to synthesize PEG hydrogels. These are synthesized via free-radical initiated chain growth polymerization. Lin & Anseth, Pharmaceutical Research, 26(3), 631-643 2009). For PEG diacrylate and dimethacrylate, the reactive chain ends free radicals are generated by photoinitiators, which can either be photocleavable or biomolecular type. Hoffman, Advanced Drug Delivery Reviews, 64, 18-23 (2012).

The mechanical strength of PEG-based hydrogels can still be compromised in vivo, and the swelling kinetics can be temporally limited. PEG superporous hydrogels enhance the swelling ratio and time. Huh, Baek, & Park, Journal of Bioactive and Compatible Polymers, 20(3), 231-243 (2005). Such modification seems essential for creating a system for countering tumor microenvironment acidity, where the acid load is not just continuous but also rapid. The addition of bicarbonate to PEG hydrogel precursors acts towards increasing the swelling rate and enhancing the pore structure of these gels. Such modification of PEG hydrogels provides an exciting avenue for not only modulating the swelling mechanics but also addressing external acidic load by the release of excessive bicarbonate within the pore structure.

Sodium bicarbonate has been used such as a pore-forming agent for PEG hydrogels. Persons having of ordinary skill in the oncological art would not know how such a hydrogel would behave towards regulating the pH in a mildly acidic environment, such as of a cancer tumor microenvironment. Pluronic F-127 hydrogels loaded with bicarbonate to regulate the tumor microenvironment pH has been tested. Goldman & Weigeri, American Journal of Gastroenterology (Springer Nature), 79(2) (1984). The test results elicit curiosity into a similar performance using PEG hydrogels.

The inventors previously modified gellan hydrogels prepared by ionic crosslinking using calcium chloride (CaCl) and embedded with sodium hydroxide (NaOH) were examined for their pH modulating capabilities in solutions of harsh to moderate acidity. The cumulative hydroxide ion release was calculated from the pH change. An environment simulating the acidity conditions of tumor microenvironment tested the response of these hydrogels, by adjusting the pH of deionized water using set amount of hydrochloric acid (HCl). For the test, an average starting pH of 6.5 was accepted as the acidic cancer extracellular pH, and the hydrogels were allowed to respond to the acidity, with fixed amounts of regular acid added at different time intervals to mimic the production of lactate by the cancer cells.

These hydrogels regulated pH at natural physiological levels for at least five days. pH control via NaOH-modified gellan gum hydrogels over five days. The hydrogels lacked mechanical integrity, with a Young's modulus of 30 kPa. An exchange of the crosslinker $Ca^{2+}$ ions with monovalent ions encountered in the physiological conditions would further affect the strength of the gels.

While regulation of an engineered acidic environment using these hydrogels was possible, using hydroxide possesses unavoidable limitation owing to its cytotoxic nature. Choi et al., BioTechniques, 66(1), 40-53 (2019).

To counter the low stiffness and the lack of a biocompatible pH regulating reagent, a few major modifications were made in the hydrogel system. Sodium bicarbonate was incorporated as a chemical modification in developing gellan hydrogels.

A biocompatible synthetic polyethylene glycol (PEG) hydrogel was included to test and contrast the use of both a natural and a synthetic hydrogel for such tumor microenvironment acidity manipulation.

A proof-of-concept assay was set up with the synthesis of gellan and PEG hydrogels modified with 100 mM sodium bicarbonate and tested in the set system of deionized (DI) water for their ability to regulate the pH. Sodium bicarbonate modified hydrogels could resist a big pH change in a mildly acidic environment, even when additional acid was added to lower the pH. The negative control is a system with no hydrogel.

To study the diffusion of bicarbonate, a system of deionized water worked well. T better simulate the cancer tumor microenvironment, an acidic solution of phosphate buffered saline was selected to examine the pH regulation using the selected hydrogels. Acidic deionized water was used to compare the behavior of hydrogels in solvents with and with no ions present. A pH of 6.5 was accepted as the average tumor microenvironment acidic pH, as compared to the normal extracellular pH of 7.4.

To test the effect bicarbonate concertation on the pore structure of PEGDA based hydrogels and testing their efficacy to regulate an acidic tumor microenvironment, photo-crosslinked PEGDA gels were synthesized and tested and compared against the natural hydrogels (gellan gum). This assay therefore aims to quantify the pH effect of bicarbonate-modified natural (gellan gum) and synthetic (PEGDA) hydrogels in a simulated acidic tumor microenvironment, while characterizing significant hydrogel properties and doing a cell proliferation and viability study on a particularly aggressive breast cancer cell line. MDA-MB-231.

Modified gellan gum hydrogels. gellan hydrogels were prepared by mixing a prepolymer Gelzan solution (2 wt. %) with an ionic cross-linker. Calcium chloride (CaCl) was added in a concentration of 2.25 mM as the crosslinking agent to enhance the mechanical stiffness of the hydrogel. To this, sodium bicarbonate ($NaHCO_3$) was added in various amounts to account for final concentrations of 50 mM, 100 mM, and 200 mM in the solution. The solution was homogenized by mixing thoroughly at a temperature of 120° C. and then allowed to cool down allowing the crosslinks to form. Hydrogels were stored at 4° C.

Gellan hydrogels are thus described according to the bicarbonate concentration with which they were synthesized. Gellan 50 implies gellan hydrogels prepared with 50 mM sodium bicarbonate.

Modified PEG hydrogels. PEG hydrogels were prepared via free-radical chain photo-polymerization. Chasse et al., Macromolecules, 45(2), 899-912 (2012). Polyethylene glycol di-acrylate (PEGDA Mn 700 Da) pre-polymer solution was created at 10 weight %. Irgacure-2959 (2-hydroxy-4'-(2-hydroxyethoxy)-2-methylpropiophenone), a type-I photo-initiator was prepared by creating a 25 weight % solution in 70% Ethanol, and then mixed with PEGDA solution to get a final concentration of 0.5 weight %. To this prepolymer mixture, sodium bicarbonate was added in various amounts to account for final concentrations of 50, 100, 200, 400, 600, and 800 mM respectively. The solution was vortexed and irradiated under ultraviolet light at a wavelength of 365 nm, roughly at 10 cm and an intensity of 5 mW/$cm^2$ until crosslinking was complete. The gels were stored at 4° C. PEG hydrogels are hereafter referred according to the bicarbonate concentration with which they were synthesized. PEG 50 implies PEG hydrogels prepared with 50 mM sodium bicarbonate.

Selection of solvent. Deionized (DI) water was used to check pH regulation affected by hydrogels. To better simulate the in vitro tumor conditions, a tumor microenvironment fluid solution was prepared by adjusting the pH of phosphate-buffered saline to 6.5. A volume of 15 mL was fixed for all the release profiles and pH control assays.

At first, cell culture media Dulbecco's Modified Eagle Medium (DMEM) was also tested. Dulbecco's Modified Eagle Medium is a cell culture media containing nutrients and buffering agents meant to simulate the composition of cell's physiological environment. Preliminary pH control using gellan 50 and Gellan100 showed that intrinsic buffering affect brought about by the media would have confounded any effect produced by the treatment hydrogels.

Albeit Dulbecco's Modified Eagle Medium would have provided a more accurate physiological condition, all the pH assays were conducted only in deionized water and phosphate-buffered saline. The way the pH adjustment was done in these solvents was by using 8M concentrated hydrochloric acid (HCl) of appropriate amount.

All the assays and characterization described hereafter were conducted in at least triplicate (n: 2'. 3).

Release profile assay design. Hydrogel samples (dimensions 7.5 mm×7.5 mm) were punched out using a biopsy punch from the prepared hydrogel discs. The gel samples were placed in the acidic solutions, and the pH was observed regularly for the first eight hours, and then every twenty-four hours up to five days.

pH control assay design. For all the pH control assays, the media volume of 15 mL was used, and pH set to 6.5 before placing the gel samples. A short-term behavior of the bicarbonate effect from the gels was observed by re-setting the pH back to 6.5 by adding HCl every hour for two hours. A long-term behavior was analyzed by re-adjusting the pH of the gel solution to 6.5 every twenty-four hours till 5 days.

Swelling kinetics. To study the swelling of as prepared hydrogels, a solution of phosphate buffered saline containing monovalent ions at a pH of 7.4 was used. Hydrogel sample punch-outs of dimension 7.5 mm×10 mm were put into a solution volume of 15 mL for seven days to attain equilibrium swelling. After 7 days, gels were taken out, blotted to remove excess solution from the surface, and weighed to get the swelled weight of the samples. The gels were dried in the oven for twenty-four hours at 80 C and weighed after to get the dry weight of the samples. These weights were used to analyze the equilibrium water content and swelling ratio of the gel samples, which was then used to analyze Flory-Huggins parameter for the hydrogel-solvent interactions.

Mechanical assay. As prepared hydrogel discs of dimensions 25 mm diameter and 10 mm height were subjected to com-pressive force on MTS Servohydraulic Dynamic Testing machine using a low-load 125 N cell. Com-pression was performed normal to the hydrogel cross-sectional area at a strain rate of 15% over sixty seconds. All the compression tests were performed at room temperature. Stress-strain curves obtained from compression were used to calculate compressive modulus. The effects of the two factors of polymer concentration (for PEG) and bicarbonate concentration (for PEG and gellan) were analyzed on the mechanical performance of the gels.

Shear oscillatory tests were done on PEG and gellan hydrogel samples of dimension 1.5 mm×40 mm to understand their rheological properties on an ARES-G2 Rheometer (TA Instruments). Oscillatory frequency sweep assays were done within the linear viscoelastic regime at a strain of 5%, a plate gap of 1400 μm, and between angular frequency of 0.1-100 rad/sec. Frequency sweeps were performed at a temperature of 37° C. for assessing the hydrogel response in an environment closer to physiological conditions.

Cell viability. Incubated MDA-MB-231 cells were passaged from a confluent T-flask into a 12-well culture plate, and the treatment hydrogels were added. For the viability study, the effect of modified PEG hydrogels bicarbonate concentrations of 200, 400, 600, and 800 mM was analyzed along with the control group with no treatment (bicarbonate), and a vehicle control of PEG with no bicarbonate. The cells were imaged every twenty-four hours under Nikon TS 100 inverted light microscope attached with Excelis HD camera and processed using an ImageJ image processing macro (performed by Gavin Mays) to estimate cell confluency from the imaged area coverage. At the end of day 5, the number of live and dead cells were estimated by Trypan staining and cell counting using a hemocytometer. Percentage viability was calculated from the number of live cells as a fraction of total cells.

Commercially Available Reagents that can be Used in the Practice of the Invention Bleach. CL030966CT, Clorox.

Clidox-S Base. 96118F, Pharmacal Research Laboratories.

Clidox-S Activator. 95I I 8F, Pharmacal Research Laboratories.
Deionized Water. 6442-88, EMD Millipore.
Doxorubicin Hydrochloride. D4193-25MG, TCI Chemicals.
DMEM (Dulbecco's Modified Eagle's Medium). 12-741F, Lonza.
FBS (Fetal Bovine Serum). 10803-034, Avantor Seradigm.
Calcium Chloride Dihydrate. 30150, Chem-Impex International.
Carbon Dioxide. CD USP50, Airgas.
DMSO (Dimethyl Sulfoxide). 023 I-500ML, VWR.
Ethanol (70%), experimental quality, E505-4L, VWR.
Disinfectant, BDHI 164-4LP, VWR.
Gellan hydrogels: Gelzan. G024-500GM, Caisson Laboratories. Gellan gum (Gelzan™ CM), sodium bicarbonate (S5761, BioReagent), and calcium chloride dihydrate (ACS reagent, >99%) were purchased from Millipore Sigma.
Hydrochloric Acid (24.5-25%). 07104-2.5L, Sigma-Aldrich. Hydrochloric acid (HCl puriss 24.5-26%), Dulbecco's phosphate buffered saline, modified (DPBS), and potassium chloride solution (BioUltra, 3 Min $H_2O$) were also purchased from Millipore Sigma.
Irgacure-2959 (2-Hydroxy-4'-(2-hydroxyethoxy)-2-methylpropiophenone). 410896-10G, Sigma-Aldrich.
Isopropyl Alcohol. BDHI 133-ILP, VWR.
Liquid Nitrogen. NI NF230LT22, Airgas.
MDA-MB-231 Triple-Negative Breast Cancer Cell Line. HTB26D, ATCC.
MTT Assay Kit (I0X stock MTT and stock solubilization solution). MT0I000, OZ Biosciences.
P-S (I00X) (Penicillin-Streptomycin). K952-100ML, VWR.
pH 4.01 Buffer. 910104, Thermo Scientific.
pH 7.00 Buffer. 910107, Thermo Scientific.
pH 10.00 Buffer. 910110, Thermo Scientific.
pH Electrode Storage Solution. 910001. Thermo Scientific.
Sodium bicarbonate. S5761-500G, Sigma-Aldrich.
Trypan Blue (0.4%). K940-I OOML, VWR.
Trypsin (0.05%)-EDTA (0.1%) (Ethylenediaminetetraacetic acid). 118-087-721, Quality Biological.
Commercially Available Materials that can be Used in the Practice of the Invention
BP80, Royaltek.
Cell Culture Flasks (vented).
T-75, 82050-856, Greiner Bio-One.
T-25, 82051-074, Greiner Bio-One.
Cell Culture Well Plates. 12-wells, 665-180, Greiner Bio-One.
Cell Culture Well Plates. 24-wells, 662-160, Greiner Bio-One.
Petri Dish (glass, 60 mm×15 mm). 75845-542, VWR.
Petri Dish (polystyrene, 60 mm×15 mm). 75845-542, VWR.
FB0875713A, Fisher Scientific.
Microplate Reader (SpectraMax). M3, Molecular Devices
Microscope (inverted light). TS100, Nikon.
Microscope Camera (Excelis HD). AU-600-HD, AccuScope.
pH Meter and Probe, 30266626, Mettler Toledo.
Hydrogel formulation. Hydrogel punch-outs—dimensions 7.5 mm×7.5 mm—were used for all pH control assays.
Mechanical testing. Compression testing of the hydrogel discs was performed on Landmark® Servohydraulic Test Systems by MTS. The sample dimension for which was 56 mm×10 mm. Rheological testing was performed on ARES-02 Rheometer by TA Instruments—the sample dimension for which was 40 mm×1.5 mm.

The compressive modulus was calculated from slopes of the stress-strain curves obtained. Data was recorded for three data points each second. The strain rate of 15% was subjected during a time of sixty seconds.

Cell media pH. The cell media pH was measured after viability study to check the effect of bicarbonate. Generally, pH increased with increasing bicarbonate in the treatment group, however the very basic pH was also observed in control group with no gels which warrants investigation.

The following EXAMPLES are provided to illustrate the invention and shall not limit the scope of the invention.

Example 1

Release Profiles

The invention provides a solution to the problem by combatting this rapid acid production and affect tumor growth by providing a delivery method to reduce metastases. The invention provides a way to actively modulate system pH with wide-reaching impact. The invention consists of a hydrogel or other soft polymer containing the desired amount of acid or base and then releasing this acid or base to the environment based on the external environment pH and the desired pH control needs. The gel or polymer is placed in a solution with a different pH to release acid or base until equilibrium pH is reached. At this time, if the pH of the solution is changed by external factors, the gel diffuses more of the acid or base to counter these effects and keep the environment at the equilibrium pH.

These gel or polymer-based systems are easy to make. Depending on the need, the systems can be made in varying sizes from a couple of millimeters to particles with submicron length scales.

The invention presents a soft material system to actively control the pH of a solution. These systems can be designed and fabricated by varying sizes or soft materials type and varying concentration according to the use requirement.

The inventors constructed gels with these characteristics.

Gellan hydrogels. Modified gellan hydrogels were prepared with the bicarbonate concentrations of 50, 100, 200, and 200 mM without $Ca^{2+}$ crosslinker. Because a higher concentration of bicarbonate resulted in uncontrolled gelation, 200 mM was set as the high point. Two control groups eliminated any pH changes produced by the solvent itself, or the gels. One used no gels as solvent control. One used gel with no bicarbonate as vehicle controls.

The inventors performed assays that showed that gellan gum gel maintains >50% structural rigidity (for at least thirty minutes swelling) at and below 0.4% w/v NaOH, gellan gum gel modulus E decreases with increasing elapsed trial time, polymer concentration, and sodium hydroxide concentration.

Basic media: Input of NaOH-loaded gellan gum gels increase $pH_{initial}$ (10.5-10.7) and gels properly respond to acid inputs to maintain $pH_{initial}$.

Neutral media: Input of HCl-loaded gellan gum gels decreases $pH_{initial}$ (7.5) and gels respond to base inputs to maintain 7.0-7.5 pH. Input of NaOH-loaded gellan gum gels increased $pH_{initial}$ (6.5-6.7) to healthy pH (7.5); pH 6.9-7.1 is held.

Neutral and basic media: Results observed with NaOH content ranging from 0.009-0.4% w/v and HCl ranging from 0.005-0.25% w/v; high concentration gels respond to greater acid/base inputs at expense of lower modulus E.

No significant visual defects or disintegration observed on NaOH-loaded GG gels after day-long trials; maintains cylindrical shape even when swollen.

Diffusive Threshold: A bicarbonate release plateau was reached within the first hour in deionized water, and thereafter the pH levels remained unchanged. Gellan gum gel's stimuli-responsiveness was terminated after 50-60% of initial NaOH content diffuses out the gel.

For phosphate-buffered saline, the time reach a pH plateau increased with the increasing bicarbonate concentration. Gellan200 without $Ca^{2+}$ increased the pH slightly more than Gellan200 during the first twenty-four hours, however the difference was not significant after three days.

Both deionized water and phosphate-buffered saline, vehicle control hydrogels with no bicarbonate modification did not affect the solution pH, even though some fluctuations were measured in deionized water, which can be attributed to the difficulty in reading the pH because of its low ionic stability. An ionic strength adjustment solution of potassium chloride, 3M at a concentration of 0.5 volume %, was added in deionized water to enhance its ionic activity without affecting the pH.

There was no affect in pH due to both the solution itself and blank hydrogels. The pH regulation was a direct consequence of the bicarbonate-modified gels.

For phosphate-buffered saline, the time reach a pH plateau increased with the increasing bicarbonate concentration. Gellan200 without $Ca^{2+}$ increased the pH slightly more than Gellan200 during the first twenty-four hours. The difference was not significant after three days.

For both deionized water and phosphate-buffered saline, vehicle control hydrogels with no bicarbonate modification did not affect the solution pH, even though some fluctuations were measured in deionized water, which can be at-tributed to the difficulty in reading the pH because of its low ionic stability. An ionic strength adjustment solution of potassium chloride, 3M at a concentration of 0.5 volume %, was added in deionized water to enhance its ionic activity without affecting the pH.

There was no effect in pH due to both the solution itself and blank hydrogels. The pH regulation was a direct consequence of the bicarbonate-modified gels.

PEG hydrogels. Modified PEG hydrogels were prepared with the bicarbonate concentrations of 50, 100, 200, 400, 600, and 800 mM. Two control groups were established like gellan to eliminate any pH changes produced by the solvent itself, or the gels. One used no gels as solvent control. One used gel with no bicarbonate as vehicle controls. Vehicle control established no effect of gel itself. A bicarbonate release plateau was reached within five days in phosphate-buffered saline, but only within eight hours in deionized water.

A bicarbonate concentration as high as 800 mM only raised the pH of phosphate-buffered saline to 9, while deionized water showed a rapid pH increase of greater than 9 with a concentration of 200 mM. Bicarbonate diffusion out of the gels could be slower in phosphate-buffered saline, despite a similar $H^+$ ions gradient to drive it, due perhaps to a steric hinderance provided by the ions present in it. Preparing equal amount bicarbonate solutions in deionized water and phosphate-buffered saline resulted in different pH changes in these solutions, indicating the $pK_b$ of bicarbonate might be different in both, and the action of phosphate ions in phosphate-buffered saline towards buffering the solution pH.

To establish a correlation between the pH of the solution (deionized water or phosphate-buffered saline), and the effective bicarbonate concentration present, a study to determine the dissociation constant, and subsequently $pK_b$, of sodium bicarbonate would need to be done.

Gellan hydrogels. To understand how the hydrogels would behave in tumor microenvironment acidity where a continuous acid load is generated by the cancer cells, the gels were provided with continuous acid supply such that the solution pH was re-adjusted to its starting point of 6.5. A short-term behavior of the hydrogels was observed by providing an acid supply at hours 1 and 2 to adjust the pH to 6.5, and thereafter adjusting it every twenty-four hours for five days.

The assays were slightly modified for the case of pH control using gellan hydrogels in phosphate-buffered saline. The net pH changes due to 50 mM and 100 mM hydrogels in phosphate-buffered saline are insignificant within the short-term two-hour range. The acid supply was only provided after twenty-four hours and subsequently each day till five days. In deionized water, the hydrogels regulated the pH both short-term and long-term by maintaining it around pH 7, even after a continuous acid load provided.

PEG hydrogels. PEG hydrogels worked excellently in manipulating the acidic environment in deionized. Even though from the release profiles, pH change went slightly higher with the bicarbonate concentration, in the pH control all concentrations worked similarly. Both short term and long term, the pH was maintained between 6.7-7.2 by the hydrogels.

An important observation in the performance of both PEG and gellan hydrogels was that pH levels are not indicative of the ability of the gels to behave towards pH change. A gel made with higher bicarbonate concentration is more resistant to pH change if an acid load occurs than a gel with lower bicarbonate concentration, even when both the solutions are at the same pH. After day 1, if solutions containing PEG 50 and PEG 100 are at the same pH of say 7. PEG 50 would require much less acid to adjust its pH to 6.5 than PEG 100.

This behavior was also observed for gels made with same bicarbonate concentration but at different days. If the solution containing PEG 100 was at the same pH after day 1 and day 2, day 2 would require a much less acid volume for adjustment to 6.5. Both bicarbonate concentration and history of acid loads factor into the buffering ability of hydrogels when faced with pH change.

Swelling kinetics. The mass swelling ratio. $Q_m$, was calculated from the swollen and the dry weight of hydrogels, where swollen weight was measured after equilibrium swelling was reached.

Swelling kinetics. Gellan hydrogels. Gellan hydrogels with varying bicarbonate concentrations were evaluated for their swelling capacities. All the gels were allowed to swell in phosphate-buffered saline at pH 7.4 for seven days until equilibrium swelling was reached, after which they were oven dried at 80° C. for twenty-four hours.

Hydrogels made without $Ca^{2+}$ crosslinker (Gellan200 without $Ca^{2+}$) degraded in phosphate-buffered saline at the end of seven days.

Gellan hydrogels lost their cylindrical shapes and collapsed into dry mass after taking out of the oven, which could be due to their very high-water content. This cause was verified by calculating the equilibrium water content (EWC) for gellan. The EWC for gellan is between 98.8-99.4% for all formulations. EWC reduced significantly ($p<0.002$) as the bicarbonate concentration went up. The swelling ratio also decreased ($p<0.001$) with the increasing bicarbonate concentration. This implies bicarbonate contributes to a higher gel stiffness in gellan because a higher stiffness corresponds to a lower ability to swell and retain water. This could be due to $Na^+$ monovalent ions from sodium bicarbonate, leading to enhanced crosslinking due to increased electrostatic attraction between the acyl links in the polymer chains.

Swelling kinetics. PEG hydrogels. PEG hydrogels with different formulations were tested for their swelling properties like gellan, but to check the effect of two factors—bicarbonate concentration and PEGDA weight %. A study of their network parameters was done using Flory-Huggins theory to quantify the swelling kinetics and network chain structures.

The equilibrium water content (EWC) increased with the increasing bicarbonate concentration—from 91% to 93.5% for PEG 0 to PEG 800. Bicarbonate concentration has a statistically significant effect on EWC ($p<0.002$) compared with the control formulation with no bicarbonate (PEG 0).

The swelling ratio went up from 10 to 14 from PEG 0 to PEG 800, with bicarbonate factor playing a significant effect. This can be explained by probable pore-forming effects brought about by bicarbonate in the network structure of a hydrogel. Malana, Bukhari, & Zohra, Designed Monomers and Polymers, 17(3), 266-274 (2014). A higher porosity correlating a higher solvent uptake and therefore swelling. Callaway, Hendrickson, Bond, Lee, Sood, & Jang, ChernPhysChem, 19(13), 1655-1664 (2018). Sodium bicarbonate has been shown to act as a pore-forming agent by reacting with the acrylate groups on PEG polymer chain, giving off carbon dioxide responsible for the enhanced porosity. Canai & Peppas, Journal of Biomedical Materials Research, 23(10), 1183-1193 (1989). The pH influences equilibrium swelling of methacrylate-based hydrogels, causing an increase in water uptake from acidic to basic solutions. Tang, Tung, & Zeng, Carbohydrate Polymers, 29(1), 11-16 (1996).

PEGDA concentration had an inverse effect on the swelling kinetics of PEG, which is expected because of a higher density of polymer chains at a higher concentration. PEGDA weight % was compared at a fixed bicarbonate concentration (200 mM) for three levels (10%, 20% and 30%). EWC and swelling ratio reduced significantly with increasing PEGDA concentration ($p<0.001$).

Gellan not only displayed much higher swelling ratio, but also an inverse effect due to different chemistries of sodium bicarbonate with PEG and gellan polymer chains.

Mechanical testing. PEG hydrogels. The compressive modulus for the hydrogel samples was calculated from the stress-strain curve obtained within the strain rate of 15%. For PEG, the modulus decreased with an increasing bicarbonate concentration, with an average value of 57 kPa for PEG 0 to 26.3 kPa for PEG 800, indicating a reduction in gel stiffness due to bicarbonate. This directly agrees with the results obtained from the swelling study-increasing the bicarbonate concentration correlates with an increased formation of porous structure within the network, leading to enhanced swelling and a decreased mechanical strength.

Similarly, the PEGDA factor caused a significant increase in the modulus ($p<0.001$), leading to a steep rise with the concentration, confirming the results obtained from swelling studies.

This highlights the tunability of mechanical properties of these hydro gel co-factored by bicarbonate and PEGDA concentrations, allowing wide range of applications ranging from soft tissues to tumors to bones.

The storage modulus varied between 300-450 Pa and was higher than the loss modulus due to a higher elastic contribution from network chains.

Conclusion. Developing modified gellan and PEG hydrogels using sodium bicarbonate for pH regulation of an engineered acidic tumor microenvironment was successfully done. Both the hydrogel systems displayed sufficient capability to manipulate the pH to normal physiological levels, however PEG offered more favorable tunability, mechanical integrity, biocompatibility, and non-fouling properties compared to gellan.

Gellan hydrogels showed a wide range of compressive and shear modulus. These hydrogels performed well in acidic DI in pH regulation, however the bicarbonate concentration up to 200 mM wasn't enough to work well in phosphate-buffered saline. PEG hydrogels showed excellent performance in regulating the pH in both DI and phosphate-buffered saline at higher bicarbonate concentrations.

The investigation of polymer-solvent interactions using Flory-Huggins theory confirmed that bicarbonate increases the mesh size of the hydrogel network, reducing the cross-linking density. Swelling ratio showed an agreeable trend as well—increasing with increased bicarbonate concentration. The cell viability results showed the utility of a PEG-bicarbonate based anti-cancer therapeutic.

The preliminary investigation on developing bicarbonate modified gellan and PEG hydrogels and their pH regulating ability in an engineered acidic tumor microenvironment was successfully completed.

Example 2

Responsive Hydrogel-Based pH Regulation to Reduce Malignant Phenotypes in Breast Cancer Cells Introduction. The tumor microenvironment is characterized by an acidic pH which confers the expression of more malignant phenotypes in cancer cells such as increased proliferation, migration, and metabolic activity. The accumulation of acid in the tumor microenvironment is attributed to the altered metabolism of cancer cells, the greater diffusion distances for cellular byproducts to existing vasculature, and the lack of buffer for pH regulation in the extracellular space. Tumor acidosis-targeted buffer therapy is an emerging anticancer treatment to mitigate aggressive characteristics of cancer from developing, improving chemotherapy efficacy, and generating favorable conditions for proper healthy and immune cell functions.

A hydrogel has been developed for the release of buffer to regulate pH, so the need for systemic administration can be overcome and harmful side effects avoided. The release of bicarbonate buffer from the hydrogel in cell culture media was confirmed via titration and acid response assays. The hydrogels were then tested on the MDA-MB-231 triple negative breast cancer cell line through a proliferation assay, scratch test assay, and MTT assay. The base-releasing hydrogels improved the efficacy of the chemotherapy drug doxorubicin on inhibiting the proliferation, migration, and metabolic activity of breast cancer cells. The effect was more pronounced at a starting neutral pH than a starting acidic pH because the cell line was maintained at a neutral pH as opposed to an acidic pH. A favorable environment was unintentionally created for the cancer cells starting at an acidic pH by the base-releasing hydrogels. The cell line can be maintained and conditioned for survival in an artificially acidic cell culture media so the individual effect of the base-releasing hydrogel on cancer cells more representative of a tumor microenvironment under advanced acidosis can be better elucidated. Cell culture methods can also be expanded from simple 2D assays to more advanced 3D techniques that are more representative of the tumor microenvironment and can test additional harmful cancer phenotypes.

Impaired anticancer therapy efficacy. Anticancer therapies are negatively affected by the acidic pH, impairing drug uptake, increasing drug efflux from cancer cells, or altering drug metabolism. Extracellular acidity impedes chemotherapy drug uptake into cancer cells. The difference in pH levels between the acidic tumor microenvironment and basic cancer cells reduces the partitioning of weakly basic chemotherapy drugs inside the cancer cell where it can act, a phenomenon known as ion trapping.

Release buffer therapy for pH regulation. The release of a buffer to counteract the acidity of the tumor microenvironment could be the solution to the negative side effects due to systemic buffer administration. Slowing the release of buffer can be achieved through incorporation of the buffer into a hydrogel that can release it in response to the acidification of the local environment. Hydrogels have been investigated for their capabilities to accomplish a buffer release to regulate pH.

Gellan gum. Gellan gum is a natural polysaccharide used as a drug delivery vehicle. Gellan gum is gaining increasing interest for biomedical applications due to its easy availability, biocompatibility, simple gelation, tunable elasticity, thermal stability, and acid reliability. Milivojevic et al., In: Natural Polysaccharides in Drug Delivery and Biomedical Applications (Elsevier Science & Technology, London, United Kingdom, 2019), pp. 145-186. Gellan gum hydrogels are stable and swell at low pH. Zia et al., International Journal of Biological Macromolecules, 109, 1068-1087 (Apr. 1, 2018). The stability of gellan gum under acidic conditions makes it an attractive candidate for buffer release for pH regulation in the tumor microenvironment. Gellan gum hydrogels, microcapsules, and films have been used in anticancer therapies using the active chemotherapy agents methotrexate, doxorubicin, and clioquinol. Zia et al., International Journal of Biological Macromolecules, 109, 1068-1087 (Apr. 1, 2018).

Previous applications in anticancer therapy are another advantage gellan gum has for release of buffer for pH regulation. Another attractive possibility is combination buffer therapy and chemotherapy in a gellan gum hydrogel vehicle.

Polyethylene glycol (PEG). Polyethylene glycol (PEG) is a synthetic nonionic polymer with many biomedical applications such as drug delivery, bioconjugation, biosensing, imaging, and tissue engineering because of its high solubility, biocompatibility, and high tolerance. Hoang Thi et al., Polymers (Basel), 12(2), 298 (Feb. 2, 2020). pH-responsive PEG hydrogels with chemotherapies incorporated have been developed for improved anticancer therapy. Chatterjee & Hui, In Hydrogels: Smart Materials for Biomedical Application (IntechOpen, London, United Kingdom, 2019), p. 15.

Before a pH of 6, PEG hydrogel swelling increases with pH. Betancourt, Pardo, Soo, & Peppas, Characterization of pH-responsive hydrogels of poly(itaconic acid-g-ethylene glycol) prepared by UV-initiated free radical polymerization as biomaterials for oral delivery of bioactive agents. Journal of Biomedical Materials Research Part A, 93(1), 175-188 (Apr. 1, 2011). PEG hydrogel swelling changes in response to pH outside the range of the physiological pH (7.4) and tumor microenvironment pH (6.5). Fine tuning the pH response of PEG conjugated nanoparticles can be accomplished between pH of 6.5-7.4 to improve the efficacy of PEGylated anticancer drugs. Hoang Thi et al., Polymers (Basel), 12(2), 298 (Feb. 2, 2020). The final ultraviolet curing process gels PEG into a uniform hydrogel, which is advantageous for avoiding microbial contamination during fabrication.

MDA-MB-231. The triple-negative breast cancer cell line MDA-MB-231 was chosen for the cell culture work with the base-releasing hydrogels. Triple negative means the MDA-MB-231 cells do not express the estrogen receptor, progesterone receptor, and the human epidermal growth factor receptor HER-2/Neu. Chavez, Garimella, & Lipkowitz, Breast Disease, 32(1-2), 35-48 (Dec. 30, 2010). This triple negative phenotype makes the cell line hard to treat because many therapies target these receptors, so MDA-MB-231 are frequently studied because of their aggressive and invasive behavior. Holliday & Speirs, Breast Cancer Research, 13(4), 215 (Aug. 12, 2011).

Hydrogel pH regulation. How much acid to add to DMEM to obtain a 6.5 pH? The answer was first determined by titration of DMEM with hydrochloric acid. At t=0, hydrogels added to DMEM. At t=ten, thirty, and fifty minutes, hydrochloric acid added to DMEM to bring pH to 6.5. At twenty-four hours after t=0: hydrogel with buffer pH=7.9, controls pH=7.5.

The release of bicarbonate by hydrogels increases the pH of the cell culture media to the desired level and improve the efficacy of the chemotherapy drug doxorubicin on MDA-MB-231 cell cultures as measured by inhibiting cell proliferation, cell migration, and metabolic activity.

Dulbecco's modified Eagle's medium (DMEM) is a liquid formulation containing salts, glucose, amino acids, and vitamins designed to support cell growth in culture. It also contains sodium bicarbonate to buffer the pH of the solution to a neutral level in a 37° C. and 5% $CO_2$ incubator, counteracting the H+ and H+-equivalent byproducts of the cells. DMEM is supplemented with 10% fetal bovine serum (FBS) to promote cell attachment, growth, and proliferation. And DMEM can also be supplemented with 1% of the antibiotics penicillin-streptomycin (P-S) to prevent bacterial contamination within mammalian cell culture. The human breast cancer cell line being investigated in the buffer release therapy to regulate pH trials will be grown using the cell culture medium of DMEM+10% FBS+1% P-S. Accomplishing this can be done by titrating the media with hydrochloric acid (HCl). The pH of DMEM is already at the physiological levels of the body, 7.4. The FBS and P-S do not affect the pH, although pH does influence the effectiveness of the antibiotics, so they were not included in the titration of DMEM. Michl. Park, & Swietach. P. Communications Biology, 2, 144 (Apr. 26, 2019). The flowchart developed by Michl, et al. for adjusting the pH of cell culture media was followed and the only requirement was to reduce the concentration of bicarbonate ions through adding HCl. Michl, Park, & Swietach, Communications Biology, 2, 144 (Apr. 26, 2019). The titration assay tried to determine the HCl needed to reduce the pH of DMEM to a pH of 6.5.

Evaluation of the hydrogel buffer therapy's pH regulation function is also needed to validate the bicarbonate release in response to introducing acid to the environment for the purpose of neutralization. Testing the hydrogels in DMEM is a necessity to verify if the release of bicarbonate function in the cell culture media which already contains sodium bicarbonate. DMEM was used with sodium bicarbonate already in solution to compare the function of the hydrogel in culture to physiological conditions where buffers exist within tissue. This allowed for comparison between the buffering capacity of the controls and the base-containing hydrogels. Understanding the bicarbonate release from hydrogel in DMEM is important for determining its function in a cell culture. The goal is to characterize the release of bicarbonate from the hydrogel in response to adding an acid to the DMEM. This assay would mimic an accelerated process of media acidification, with the source of acid being manually added HCl instead of cellular byproducts. The release of bicarbonate by the hydrogel in a cell culture can be inferred from the artificial process.

Materials and methods. DMEM was titrated with HCl according to the following procedure. 50 mL of DMEM with a sodium bicarbonate (NaHCQ3) concentration of 44.042 mM was added to a beaker containing a magnetic stir bar and placed on a magnetic stirrer hot plate. The stirring was set to the lowest setting and heat set to maintain a temperature of 37° C. A pH meter with an electrode in storage solution was then calibrated according to the instruction manual using standard buffers for pH 4.01, pH 7.00, and pH 10.01. The pH meter and electrode were then used to measure the change in pH of the DMEM solution as 5 μL increments of 25% HCl were added. After each addition of HCl into the DMEM became well-mixed and the pH reading stabilized, the pH value was recorded. This continued until the endpoint of a total 400 μL of 25% HCl was added to the DMEM because it was sufficient to identify both the equivalence point and the volume of HCl needed for a pH of 6.5. The titration was run in triplicate to validate results.

The second step was to place the hydrogels in DMEM to validate the release of base function. The base-releasing hydrogels had a concentration of 200 mM sodium bicarbonate. The control hydrogels contained no buffer agent. 15 mL of DMEM was added to three glass vials for each case. The assays included base-releasing gellan gum hydrogel, base-releasing PEG hydrogel, control gellan gum hydrogel with no base, control PEG hydrogel with no base, and no hydrogel. For each case of hydrogel, a single 0.12 mL hydrogel was added to each vial at t=0. Nothing was added at t=0 for the case using no hydrogel. The pH of the DMEM in each vial was recorded every five minutes using a pH meter and electrode. 25% HCl was added to each vial at ten minutes, thirty minutes, and fifty minutes. The HCl was added in volumes needed to reduce the pH down to 6.5 based on the previous titration of DMEM. The first addition of 25% HCl at ten minutes was 19.4 μL for the gellan hydrogels and 19.0 μL for the PEG hydrogels. The next addition of 25% HCl at thirty minutes was 6.6 μL for the gellan hydrogels and 6.1 μL for the PEG hydrogels. The final addition of 25% HCl at thirty minutes was 7.4 μL for the gellan hydrogels and 7.3 μL for the PEG hydrogels. The same amounts were added to the control assays for the corresponding hydrogel. Measurements at 5-minute intervals ceased after 115 minutes passed. After twenty-four hours from t=0, the pH of each solution was measured again to determine how it finally stabilized. Three trials of each case were performed for statistical validation of results.

For the data for the acid-base titration of 50 mL of DMEM (44.042 mM NaHCO$_3$) with 25% HCl. The equivalence point was identified as 200 μL of 25% HCl in 50 mL of DMEM for an average pH of 3.52±0.77. Adding 85 μL of 25% HCl to 50 mL of DMEM achieved a pH of 6.49±0.06. From these data the volume of 25% HCl to add to any volume of DMEM (when above a pH of 6.5) to obtain a pH of 6.5 can be approximated.

The base release profiles of both gellan gum and PEG hydrogels in DMEM changed in response to the environment. When hydrogels were initially introduced to the DMEM, the pH rose in both assays, signaling release of the bicarbonate from the hydrogel. The increase in pH of the control assays were due to the existing sodium bicarbonate buffer in the DMEM. There was an average increase in pH of 0.27 for the base-containing gellan gum hydrogels and 0.25 for the base-containing PEG hydrogels after its addition to a neutral pH DMEM. Upon the first addition of acid to the base-containing trials, the pH dropped drastically from about 7.79±0.02 to 6.69±0.03 for gellan gum and from 7.77±0.04 to 6.67±0.03 for PEG. 20 minutes after the first dose of acid, the pH had rose to 6.94±0.03 for gellan gum and 6.90±0.05 for PEG. Between t=15 and t=30, the pH increased by an average of 0.24 for both base-containing hydrogels. After the second dose of acid at thirty minutes, the pH similarly fell to 6.75±0.05 and rose back up to 6.99±0.04 for buffer-containing gellan gum hydrogel, while it dropped to 6.76±0.01 then increased to 6.98±0.05 for buffer containing PEG hydrogel. Between t=35 and t=50, the pH increased by an average of 0.24 for base-containing gellan gum hydrogel and 0.22 for base-containing PEG hydrogel. The final addition of acid occurred at fifty minutes where the pH of DMEM for buffer-containing gellan gum dropped to 6.73±0.05 and for buffer-containing PEG dropped to 6.63±0.03. The pH recordings at the 5-minute intervals between acid additions were very similar for both the gellan gum and PEG base-containing hydrogels. After twenty-four hours, the pH of the buffered gellan gum hydrogel-containing DMEM was 7.91±0.08 and the pH of the buffered PEG hydrogel-containing-DMEM was 7.82±0.10.

This further increase in pH a day after the start of the assay further validates the release of bicarbonate by the hydrogels. The gellan gum-based hydrogel was observed to maintain the pH of DMEM slightly more basic than the PEG-based hydrogels.

The objective of the titration was to determine how the pH of DMEM can be reduced to the 6.5 pH of the tumor microenvironment. The goal was achieved because it took 85 μL of 25% hydrochloric acid to reduce the pH of 50 mL of DMEM to 6.49±0.06. The stock 7.4 pH DMEM can be modified to a desired pH using the titration data. Cancer cell behavior can be observed under both acidic and physiological pH conditions. The effect of hydrogel-based release buffer therapy on was better representative of the tumor microenvironment in the artificially acidified culture media.

The equivalence point of the acid-base titration of DMEM with hydrochloric acid was 3.52±0.771. The equivalence point is useful to illustrate the accuracy of the measurements. Outside a range of 145 μL-245 μL hydrochloric acid (corresponding pH range of 5.95-2.29) the standard deviation of the recorded pH was less than 0.2. There is greater confidence in the measurements made outside this range. The steepness of the curve and large error bars at the equivalence point is because additional amounts of acid greatly reduce the pH when there are theoretically equal moles of titrant to analyte in solution. Therefore, there is greater certainty in the measurements.

Cell proliferation assay. MDA-MB-231 breast cancer cell line. Cells given pH, hydrogel, sodium bicarbonate, and doxorubicin treatment. At twenty-four hours, cell confluency is observed and recorded via image processing. At Day 6, cell counting was performed using a hemocytometer. All assays increased in confluency. Buffer-hydrogel in 7.4 pH showed most inhibitory effect. Control-hydrogel in 7.4 pH also showed inhibitory effect. Buffer-hydrogel in 6.5 pH showed no effect. Assays without hydrogels consistent with confluency analysis. Assays with any hydrogel have low manual cell counts.

The assay introducing hydrogels and acid to DMEM was performed to determine if there is a regulation of pH by the hydrogel's release of base. In both the base-releasing gellan gum and PEG hydrogel assays, upon adding acid to DMEM to bring the pH down to that of the tumor microenvironment, the pH proceeded to gradually rise. The observed increase in pH from control assays where no hydrogels or hydrogels without sodium bicarbonate were present in DMEM can be attributed to the sodium bicarbonate already present in the DMEM. The culprit for the rising pH to levels much higher than the controls in the base-containing hydrogel assays can be attributed to the release of additional base to counteract the acid introduced to the solution.

The base-containing hydrogels have a high pH and the DMEM a pH of 7.4. When the hydrogels are introduced to the DMEM, it becomes slightly basic because there exists a pH gradient between the hydrogel and the solution. The hydrogel release base to eliminate the concentration gradient. Once an acid is fed into the DMEM, the pH gradient is reinstated. The hydrogel once again release base to neutralize the acid and halt the development of a pH gradient. This continues until all the base has been released from the acid, where eventually the acid diffuses into the hydrogel to reach a pH equilibrium between solution and hydrogel. In the context of the base-releasing hydrogels, pH regulation is defined as the release of base in response to an acid being introduced to the environment. The hydrogels are functioning as regulators of pH because base only release when the pH of its surroundings suddenly decreases, causing a gradient between the hydrogel and its external environment.

Without sufficient buffer, cancer cell cultures acidify the cell culture media. This is analogous to the tumor microenvironment where insufficient buffer contributes to the accumulation of acid. These results show that the hydrogels can increase the pH of acidic cell culture media in which cancer cells can survive. Buffer containing hydrogels can release bicarbonate to counteract the acid production of cancer cells, having a ripple effect on their malignancy.

All assays not subjected to the chemotherapy increased in confluency over the six days, while the assays treated with doxorubicin all decreased in confluency over the six days. The efficacy of doxorubicin as an anticancer treatment is known, so the cell proliferation assay results for the assays treated with I µM of doxorubicin are discussed independently from those that received no chemotherapy. Separation of the data in this manner allows for individual analysis of the direct effect of the hydrogels on the cancer cell proliferation and the influence of the hydrogels on doxorubicin efficacy as measured by cell proliferation.

First, the assays not receiving any chemotherapy drug all saw cell proliferation increase over the six-day trial period. Adding base-releasing hydrogel to cell culture media of pH 7.4 had the most inhibitory effect on MDA-MB-231 cells in both the image confluency and final cell count readings. The sodium bicarbonate released by the hydrogel elevates the pH to alkaline levels. Cancer cells do not survive as well under basic conditions. Adding base-releasing hydrogel to 6.5 pH cell culture media did not have an inhibitory effect on MDA-MB-231 cells when analyzed through image processing. The sodium bicarbonate is likely increasing the pH from acidic levels to neutral levels, providing the cells with an environment in which they have been conditioned to grow. The final three readings for base-releasing hydrogel in 6.5 pH shows no statistically significant difference when compared to the positive control. However, the final six-day manual cell count does show a statistically significant difference between this case and the positive control. Interestingly, the PEG hydrogels at both starting pH levels alone follow similar proliferation rates over the six days to the PEG hydrogels with base. This is also observed in the final six-day cell counts using the hemocytometer. There could be a possible influence of the PEG itself on the proliferation of MDA-MB-231 cells.

Next, the assays treated with 1 µM of the chemotherapy drug doxorubicin all saw cell proliferation decrease over the six-day trial period. Like the untreated trials, base-releasing hydrogel added to 7.4 pH cell culture media exhibited the greatest inhibition of MDA-MB-231 cell proliferation in both the image confluency and final cell count readings. The same explanation is relevant still, with the additional consideration that the excessive alkalinity would also improve the chemotherapy efficacy combined with the change in pH also directly inhibiting the cell proliferation. The case of base-releasing hydrogels added to 6.5 pH with doxorubicin does not seem to have similar inhibitory effects on cell proliferation to the case with doxorubicin alone added to a 7.4 pH cell culture media. Adding the base-releasing hydrogel to the slightly acidic environment inhibits cell proliferation better than the control, which differs than the trend observed in the non-chemotherapy trials. The PEG hydrogel vehicle control may also inhibit the cell proliferation or improved the chemotherapy efficacy.

The manual cell counts follow the confluency values from image processing only in assays without hydrogel. The discrepancy between the image derived confluency values and the manual cell counts for the hydrogel assays could be explained by the hydrogel possibly reducing cell proliferation through mechanical damage. A concern was that the large PEG hydrogel resting on the adhering surface would prevent a confluent monolayer from growing. The confluency calculated from the images of the monolayer would not be affected by this because the areas chosen for image taking were not near the PEG hydrogel. However, the manual cell count would be influenced by the hydrogel blocking an area of the well from cells attaching and growing. The hydrogels may inhibit the proliferation of MDA-MB-231 cells if analyzed via manual counting simply by resting on the bottom of the well and reducing the total area of the well allowed for cell attachment. The hydrogel occupies 13.1% of the surface area of the adhering surface. Accounting for this loss in surface area from the cell counts, the assays without hydrogels did not decrease to levels significant enough to change interpretation of the results. The surface area blockage may not have been the only source of physical prevention of cell growth. The hydrogel could have moved across the monolayer causing physical damage to the monolayer in an area greater than the hydrogel surface only resting on the adhering surface. The size of the hydrogel was consistent and not a variable explored in this assay. Blockage of the adhering surface must be prevented to better elucidate the effect of the hydrogel's buffer release on cell proliferation. Another strategy is minimizing the hydrogel size to prevent any mechanical damage to the cell culture monolayer.

The hydrogel inhibits cell proliferation when added to a neutral pH. Because the cell line use was not conditioned to survival in an acidic pH environment before the trial, adding base-releasing hydrogel to the 6.5 pH saw confluency values like the positive control. Another assay can test the hydrogels on low-pH-adapted MDA-MB-231 cells to better elucidate the effect of the hydrogel-based buffer therapy on cells conditioned to grow in an acidic environment. This introduces the base-releasing hydrogel to an acidic environment preferred by low-pH-adapted cancer cells, bringing the pH to a neutral level where the cell proliferation can be monitored.

Greater proliferation of MDA-MB-231 cells was observed at the neutral and acidic pH environments and minimal proliferation occurred at final alkaline pH created by the hydrogels. The doxorubicin efficacy on cell proliferation inhibition was most improved at an alkaline cell culture media pH created by the buffer-releasing hydrogels at an initial pH of 7.4. PEG hydrogels formulated without bicarbonate deserve further testing to determine any direct influence on cancer cell proliferation not related to the release of base.

Scratch test. Measures cell migration. Measures scratch confluent cell monolayer. Three images taken of scratch in each well at t=0 hours, twenty-four hours, and forty-eight hours. All assays increased scratch closure. Buffer-hydrogel in 7.4 pH showed most inhibitory effect. Buffer-hydrogel in 6.5 pH showed no effect. All assays did not exceed 75% scratch closure. Hydrogels added to 7.4 pH had no change in scratch closure between twenty-four hours and forty-eight hours.

The next malignant characteristic of cancer cells under investigation was their migration. More aggressive cancers are associated with greater migration, invasion, and metastasis. Persons having ordinary skill in the cell biological art can examine the coordinated movement of cell populations through an in vitro scratch test, also known as a wound healing assay, by creating a gap in a confluent cell culture monolayer, monitoring the migration of cells into the gap through timed microscopy imaging, and analysis through image processing software. Jonkman, Cathcart, Xu, Bartolini, Amon, Stevens, & Colarusso, Cell Adhesion & Migration, 8(5), 440-451 (Oct. 31, 2014). The scratch test assay is a simple and inexpensive method of investigating the cell-cell and cell-matrix interactions during cell migration and is easily imaged. Liang, Park, & Guan, Nature Protocols, 2, 329-333 (Mar. 1, 2007). A scratch would close slower if the treatment inhibited the migration rate of the cells. Ratio of cell migration is calculated from images as a percentage of the remaining area void of cells at time points beyond when the initial scratch was made. See Razak et al., Scientific Reports, 9, 1514 (Feb. 6, 2019). A scratch test cell culture assay of MDA-MB-231 triple-negative breast cancer cells in a microfluidic device with pH and oxygen gradients found the cells to preferentially migrate towards higher levels of pH and oxygen. Takahashi, Yamaguchi, & Yamaoka, International Journal of Molecular Sciences, 21(7), 2565 (Apr. 7, 2020). Doxorubicin has been observed to significantly inhibit the migration of the human osteosarcoma cell line U20S when compared to other anticancer drugs in a scratch test. Wang, Decker, Zechner, L., Krstin, & Wink, BMC Pharmacology and Toxicology, 20(1), 4 (Jan. 9, 2019). A greater cell migration is observed at the higher pH environments from buffer release by hydrogels and less cell migration occur when these higher pH environments improve the efficacy of doxorubicin.

Nearly all assays show an increase in scratch closure from twenty-four hours to forty-eight hours when compared to the 0% scratch closure area at 0 hours. All assays not treated with doxorubicin showed increased scratch closure over the 48-hour trial compared to their counterpart assays that did include the chemotherapy. Analysis of the scratch test results with and without chemotherapy treatment are performed independently because doxorubicin efficacy against cancer cell migration has been well characterized. The direct effects of hydrogels on cancer cell migration and the influences of hydrogels on doxorubicin-induced inhibition of cancer cell migration are investigated individually.

The assays sans chemotherapy treatment all saw increased closure of the scratch over the two-day trial period. The greatest inhibitory effect on cell migration was observed where base-releasing hydrogel was added to cell culture media of pH 7.4. This was the only case without chemotherapy treatment where the decreased percentage of scratch closure was statistically significant relative to the positive control at both time points. This was also the only non-chemotherapy case not to exceed 50% scratch closure by twenty-four hours (0.42±0.06) and 75% scratch closure by forty-eight hours (0.52±0.08). The addition of base-releasing hydrogel to the 7.4 starting pH of the cell culture media had the smallest percentage of scratch closure between the twenty-four-hour time point and the forty-eight-hour time point and over the total forty-eight-hour trial. The hydrogel releasing bicarbonate base increases the pH to alkaline levels, which is responsible for this decreased cancer cell migration (even more so than many of the doxorubicin treated trials) because the environment becomes too harsh for the cells. In comparison, inclusion of base-releasing hydrogel to the 6.5 starting pH of the cell culture media showed improved migration rates (0.71±0.17 at twenty-four hours to 0.91±0.03 at forty-eight hours) compared to the positive control (0.53±0.16 at twenty-four hours to 0.82±0.12 at forty-eight hours). This can be explained by the base-releasing hydrogel increasing the pH of the cell culture medium back up to a neutral level, creating a more favorable environment for the MDA-MB-231 cells conditioned to grow in a neutral pH cell culture media. The assays with neutral and acidic pH conditions do not alter the cancer cell migration with any statistically significance compared to the positive control. All other non-chemotherapy treatment assays had no statistically significant change in the migration of MDA-MB-231 cells relative to the positive control.

All assays treated with doxorubicin did not exceed a 75% scratch closure: the closest being doxorubicin treated control alone with no hydrogel treatments at both neutral and slightly acidic pH. All assays exposed to chemotherapy were compared to the MDA-MB-231 cells treated with doxorubicin and grown at 7.4 pH. This helped in determining if any assays had increased the efficacy of doxorubicin on inhibiting cell migration. There was no observed change in scratch closure in the chemotherapy assays from twenty-four hours to forty-eight hours at 7.4 pH treated with base-containing and base-lacking PEG hydrogels. The two hydrogel assays at 7.4 pH were the only with statistically significant less wound closure than the doxorubicin treated control. Inhibition of cell migration is much more pronounced in the case with base-containing hydrogel and doxorubicin (0.29±0.10 to 0.29±0.15) than the vehicle control hydrogel with doxorubicin (0.45±0.10 to 0.46±0.13). The doxorubicin assays with a starting pH of 6.5 all saw an increase in scratch closure from twenty-four hours to forty-eight hours. The base-releasing hydrogels introduced to the cells at a starting pH of 6.5 only caused the pH to rise to neutral levels, explaining why no statistical significance is observed from the positive control. In contrast, adding base-releasing hydrogels to the cells at a starting pH of 7.4 likely caused the pH to rise to highly alkaline levels, making the doxorubicin even more effective than at both neutral pH and acidic pH. This may not be the desired effect in the final form of the base-releasing hydrogel as a treatment because a more neutral pH would still be preferred to benefit the innate cell population and immune system in the tumor microenvironment. Increasing the pH of the tumor microenvironment to alkaline levels do not benefit healthy cells, but cancer cells can adapt to these conditions.

Scratch test trials could be conducted by conditioning a culture of MDA-MB-231 cells to grow in artificially acidic cell culture media. Using low-pH-adapted MDA-MB-231 cells better elucidate the effect of the base-releasing PEG hydrogels on a subpopulation of cancer cells conditioned to survival in acidic environments. Under the current test conditions, the bicarbonate-containing PEG hydrogels are essentially bringing the acidic pH back up to neutral levels favorable for the cancer cell's survival.

A greater migration of MDA-MB-231 cells was observed at the neutral and acidic pH environments and minimal migration occurred at final alkaline pH created by the base-releasing hydrogels. The doxorubicin efficacy on cell migration inhibition was most improved at an alkaline cell culture media pH created by the base-releasing hydrogels at an initial pH of 7.4.

MTT assay. Measures metabolic activity. Cells reduce membrane permeable salt MTT (yellow) to formazan crystals (purple). Incubate for three days with treatment. Incubate for four hours with MTT. Add solubilization solution. Incubate for twelve hours. Measure absorbance of every well at $OD_{570\ nm}$-$OD_{650\ nm}$. See Riss et al., The Assay Guidance Manual (Eli Lilly & Company and the National Center for Advancing Translational Sciences. Bethesda, MD, USA, 2016). Hydrogels added to 7.4 pH with no drug had decreased metabolic activity. Hydrogels added to 6.5 pH with drug had decreased metabolic activity. Base-releasing hydrogel reduced cell proliferation, migration, and metabolic activity at an alkaline pH. Base-releasing hydrogel improved doxorubicin efficacy against cell proliferation, migration, and metabolic activity at an alkaline pH. Neutral-pH-adapted cells prefer neutral pH.

The metabolism of cancer cells can be measured by the activity of the mitochondrial reductase enzyme. The protein catalyzed reduction of the membrane-permeable yellow salt MTT (3-(4,5-dimethylthiazol-2-yl)-2,5-diphenyltetrazolium bromide) into a purple formazan (1-(4,5-dimethylthiazol-2-yl)-3,5-diphenylformazan) crystal product through the oxidation of NADH to $NAD^+$. See Riss et al., Cell viability assays. In: The Assay Guidance Manual. Bethesda, MD: Eli Lilly & Company and the National Center for Advancing Translational Sciences (2016). The purple crystals dissolve, and the cells lyse when a DMSO-based solubilization solution is added to cells cultured in the presence of MTT. This is an endpoint assay because the cells die upon addition of this solubilization solution. The activity of mitochondrial reductase ceases upon death of the cells, so the formazan produced in a cell culture do not change. The metabolic activity of the cells in culture can be measured by this conversion of MTT to formazan crystals. The absorbance can then be recorded at $OD_{570\ nm}$ and $OD_{650\ nm}$ to quantify the formazan produced by the cells through the mitochondrial reductase conversion from MTT. Riss et al., Cell viability assays. In: The Assay Guidance Manual (Eli Lilly & Company and the National Center for Advancing Translational Sciences. Bethesda, MD, USA, 2016). The absorbance is measured spectrophotometrically via a plate reader.

All assays not subjected to the chemotherapy had metabolic activity greater than the assays treated with doxorubicin. The anticancer effects of doxorubicin are known, so the MTT assay results for the assays treated with I µM of doxorubicin is discussed independently from those that received no chemotherapy. Analysis of the data for the direct effect of the hydrogels on the breast cancer cell's metabolic activity are performed separately from the influence of the hydrogels on doxorubicin efficacy as measured by metabolic activity.

The assays not treated with doxorubicin saw decreased metabolic activity with adding hydrogel. Base-containing hydrogel added to 6.5 pH showed no statistically significant difference to the positive control because the pH likely rose to a neutral pH. The hydrogels added to 7.4 pH resulted in decreased metabolic activity. The base-containing hydrogel would have increased the pH to alkaline levels too harsh for cell survival. The metabolic activity could have been influenced similarly to cell proliferation by the hydrogel physically blocking or moving along the surface area of the adhering surface.

Assays with 1 µM of doxorubicin showed statistically significantly less metabolic activity than assays without, validating its efficacy as an anticancer agent. As expected, the doxorubicin was slightly more efficacious at the more alkaline pH created by adding the base-releasing PEG hydrogels to a starting neutral pH. Both base-containing and control hydrogels added to 6.5 pH saw improved efficacy of doxorubicin inhibiting the conversion of MTT to formazan by the cancer cells. The hydrogel bringing the cell culture medium back to a neutral pH from an acidic pH can explain this improved efficacy, however, the control PEG hydrogel with no base needs further investigation similarly to the assays not treated with the drug.

Adding hydrogel with and without bicarbonate improved the inhibition of metabolic activity in all pH and drug conditions. This furthers the urgency from the proliferation assay results to limit the contribution of the physical hydrogel to better elucidate the effect of the release buffer therapy. The MTT converted to formazan depends on the number of cells present on the adhering surface of the cell culture. The metabolic activity of the cells would be influenced by the hydrogel blocking the attachment and growth of cells to an area of the well. Using the 13.1% occupancy of the hydrogel on the surface area of the adhering surface the absorbance readings were corrected. After accounting for this loss in surface area from the metabolic activity, the assays without hydrogels did not decrease to levels significant enough to change interpretation of the results. The blockage of surface area may not have been the only physical source of preventing cell growth. The movement of the hydrogel across the monolayer could have also caused physical damage in an area greater than the hydrogel surface only resting on the adhering surface. This assay did not account for the size and movement of the hydrogel as a source of inhibiting the metabolic activity of the cells. The effect of the hydrogel's buffer release on the metabolic activity of cells cannot be determined before the sources of error due to the physical prevention of cell growth is addressed. The hydrogel can be placed into a well insert in to avoid any physical blockage or damage to the monolayer, while also allowing for proper diffusion of the base into the cell culture media. Engineering the hydrogel to a minimal size is another strategy to prevent mechanical damage to the cell culture monolayer.

The initial results identified from this assay on the direct effect of the hydrogels on MDA-MB-231 metabolic activity and doxorubicin efficacy as measured by metabolic activity can be tested. The dosage of doxorubicin can be varied to include smaller concentrations where the change in chemotherapeutic efficacy due to the buffer-releasing hydrogel is clear. The incubation time of the cells with each treatment can be shortened. The doxorubicin killed nearly all the cancer cells over the three-day trial period, especially when combined with the likely effect of physical damage from the hydrogels, so a shorter treatment period can show a decreased overall metabolic rate of the cells before too many cells die.

The metabolic activity of MDA-MB-231 cells were greatest at a neutral and acidic pH and inhibition of metabolism occurred at an alkaline pH induced by the hydrogels. The buffer-releasing hydrogels improved the doxorubicin induced inhibition of the cancer cells' metabolic activity as the pH became more alkaline. The vehicle control PEG hydrogels require further investigation to determine if their observed inhibitory effect on metabolic activity is due to its size or composition.

Hydrogel formulation. The formulation of the hydrogel in its current state is very rudimentary, essentially being a base within a PEG hydrogel. To get to this point, the gellan gum hydrogel formulation had to be adjourned for the time being because of the continued issue of contamination making it unacceptable for cell culture methods. Using PEG as the hydrogel foundation was chosen because of the final UV curing process acting as a safeguard to kill any contamination after autoclave sterilization of the ingredients.

The vehicle control assays surprisingly seemed to contribute to the inhibition of the MDA-MB-231 cell's proliferation rate and metabolic activity. This could be explained in two ways: (1) the PEG directly inhibits cancer cell activity or (2) the size of the hydrogel prevented more cancer cell proliferation. PEG was found to have an antiproliferative effect on colorectal cancer mouse models through the membrane signaling molecule, epidermal growth factor receptor (EGFR), a mediator of the Snail/β-catenin signaling pathway essential to proliferation. Wali, Kunte, Koetsier, Bissonnette, & Roy, Molecular Cancer Therapeutics, 7(9), pp. 3103-3111 (Sep. 1, 2009). EGFR is overexpressed by triple-negative breast cancers, including MDA-MB-231. Masuda et al, Breast Cancer Research and Treatment, 136(2), 331-345 (Nov. 18, 2013). The MDA-MB-231 cells could be inhibited by the PEG alone. PEG has been a hydrogel scaffold in 3D cell culture work with the triple-negative breast cancer cell line MCF-7. PEG did not negatively influence cell viability and proliferation compared to other commonly used ECM-mimicking substrates. Livingston et al., ACS Biomaterials Science & Engineering, 5(11), 6089-6098 (2019). The large size of the hydrogel resting on the monolayer seems to be the more likely contributor to the observed decrease in metabolic activity and proliferation rate because its blockage of available surface area for the cells to grow result in fewer total cells in the well. The conclusions could not be changed when the data was corrected for the lost area of the adhering surface due hydrogel blockage. The movement of the hydrogel along the monolayer likely further damaged even more area of the adhering surface than just that occupied by a static hydrogel. A trial using an inert material of similar physical properties to the hydrogel can also be performed to investigate minimizing the blockage of and damage to the adhering surface for the cells to verify the source of the inhibition in these assays as either the hydrogel size or composition. Tuning hydrogel size and shape can be done to overcome the current negative mechanical effect on cell culture growth. The fabrication of buffer-containing PEG microgels is explored as the next step to minimize a negative mechanical effect on cell culture growth. A well insert can prevent the large hydrogel from contacting the cell monolayer, while still allowing for the buffer to diffuse base into the media and engage in the pH regulation of buffer therapy. Using a well insert to contain the hydrogel in the cell culture media separately from the cell monolayer allows avoidance of halting cell culture work while micro-PEG hydrogels are developed.

The hydrogel can be manually delivered to the tumor microenvironment by implantation. The implantation can be coupled to a routine tumor biopsy procedure to avoid excessive invasive treatment. There would be no need for a second invasive procedure to remove the hydrogel from the tumor microenvironment since the biocompatible hydrogel degrades in the body naturally, without invasive procedures reserved for treatments of absolute necessity.

The PEG-based hydrogel can be further modified to encompass many other constituents for various purposes, such as including a chemotherapy within the hydrogel, specifically doxorubicin, since the current work shows evidence that the combination of the base-releasing hydrogel improves the efficacy of the drug on inhibiting the proliferation rate, migration rate, and metabolic activity of MDA-MB-231 breast cancer cells. The type of base released by the hydrogel can be further explored since buffer therapy has expanded beyond the volatile sodium bicarbonate to include non-volatile agents such as IEPA, free-base lysine, and THAM. Ibrahim-Hashim & Estrella, Cancer Metastasis Review, 38(1-2), 149-155 (2020).

Sodium bicarbonate is inexpensive, used in other biomedical applications, and a natural buffer of blood and the tumor microenvironment. Sodium bicarbonate is also difficult to test on cell culture due to atmospheric $CO_2$ buffering of media components. To maintain accurate pH measurements within physiologically relevant conditions, a 5% CO2 incubated environment must be maintained.

The results show that control hydrogels inhibiting malignant phenotypes depends upon PEG composition and size causing mechanical damage to cells.

Example 3 pH Control

The gellan and PEGDA hydrogels described in this EXAMPLE regulate the pH of acidic or alkaline solutions depending on the type of encapsulated buffer. Encapsulates diffuse from hydrogels until a pH equilibrium is established between the solution and the hydrogel. After this, additional diffusion of the encapsulate occurs as needed to counteract a change to the pH of the surrounding solution.

Figure 2A:
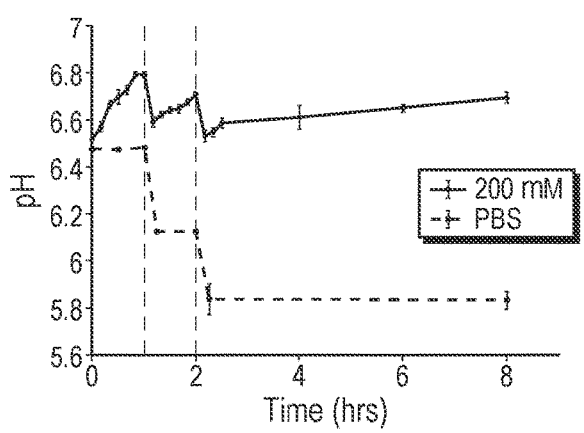
FIGS. 2A-2B are a pair of graphs showing pH change over time in $NaHCO_3$-loaded hydrogels in weakly acidic phosphate-buffered saline solutions (pH 6.5).
Figure 2B:
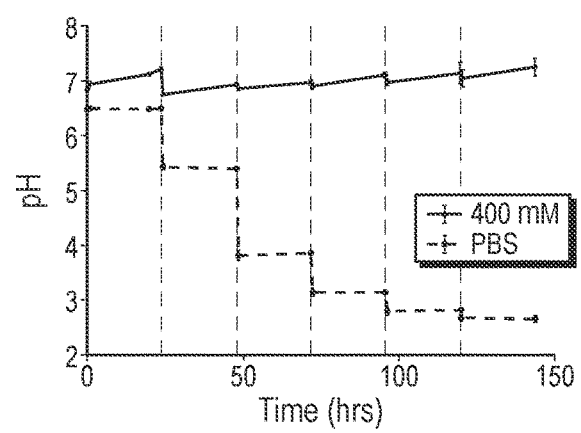
Figure 8A:
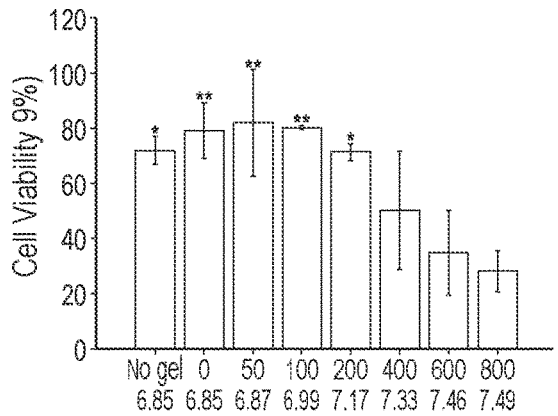
FIGS. 8A-8B are a pair of bar graphs showing that doxorubecine assays were repeated with base-eluting PEGDA hydrogels.
Figure 8B:
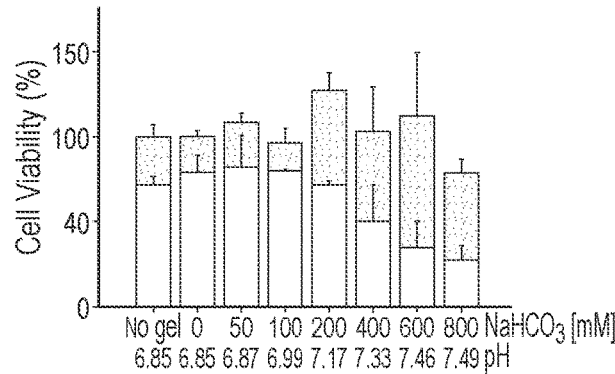
Figure 9A:
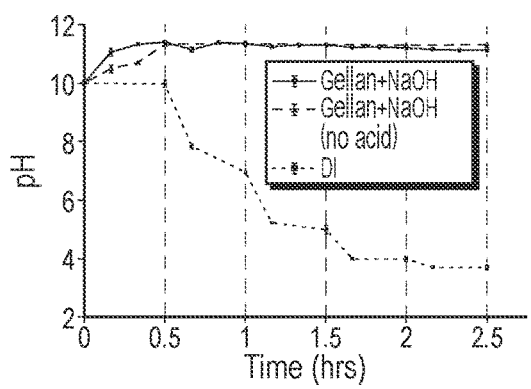
FIGS. 9A-9B are a graph showing NaOH-loaded and HCl-loaded gellan hydrogels demonstrate an ability to adjust the pH of deionized water towards an alkaline or acidic equilibrium respectively.
Figure 9B:
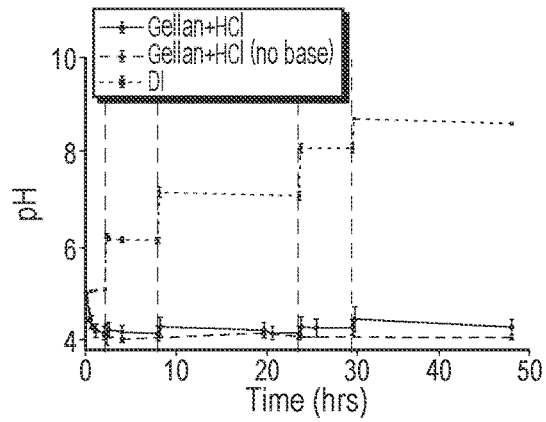

To demonstrate this effect, the pH of acidic (pH 6.5) phosphate-buffered saline solution containing $NaHCO_3$-loaded gellan or PEGDA hydrogels were measured at regular intervals over several days with periodic addition of acids in the solution. Shown over multi-hour (gellan) and multi-day (PEGDA) durations, both hydrogels perform similarly in releasing bases to regulate the solution's pH towards the desired equilibrium of pH neutrality. See FIGS. 2A-2B. Gellan hydrogels loaded with 200 mM $NaHCO_3$ increased solution pH from 6.5 to 6.8 within the first hour of introduction. See FIG. 2A. The addition of free acid solution at t=1 hour and t=2 hours caused an immediate drop in solution pH to 6.5 counteracted by the release of additional $NaHCO_3$ from the hydrogel. Similarly, PEGDA hydrogels loaded with 400 mM $NaHCO_3$ adjusted the acidic phosphate-buffered saline pH towards neutrality within one hour. See FIG. 2B. Gellan and PEGDA hydrogels could maintain a neutral pH over a week despite adding acids to the hydrogel surrounding solution every twenty-four hours. In both cases, solutions containing gellan or PEGDA hydrogels had slightly higher pH values than control solutions that did not experience hydrogel pH regulation. This is an initial release until the equilibrium concentration is established between the hydrogel and the surrounding solution. The addition of acid into the surrounding solution increased the concentration gradient between the sodium bicarbonate inside the hydrogel and the surrounding solution, stimulating the hydrogel to release more base in response to lowered pH. The addition of acids to phosphate-buffered saline control cases (without pH regulating hydrogel) caused a significant drop in pH for the assay conditions, clearly showing that maintaining pH neutrality is achieved through the hydrogel's base-eluting capability. These assays demonstrate that base-eluting gellan and PEGDA hydrogels resist the periodic addition of acids to regulate pH towards a particular equilibrium value. Gellan hydrogels could be loaded with NaOH or HCl to regulate the pH of aqueous solutions towards extreme high or low pH, respectively. See FIGS. 8A-8B. The various buffers that could be loaded into the hydrogels offer tunable functionality to meet specific applications. For biological applications, $NaHCO_3$-loaded hydrogels supplement the blood's naturally inherent $NaHCO_3$-based pH regulation system. The hydrogel's biological applications are limited only by the acids and bases that can be loaded to the hydrogel. To supplement the body's natural buffering systems, the next EXAMPLE describes $NaHCO_3$-loaded hydrogels.

Example 4

Bicarbonate Release

Figure 3A:
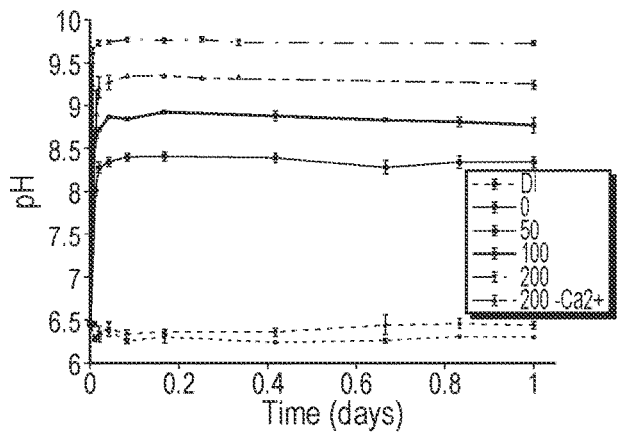
FIGS. 3A-3D are a set of four line graphs showing the pH profile of sodium bicarbonate loaded hydrogels over time in deionized water (DI) adjusted to pH 6.5 and phosphate-buffered saline adjusted to pH 6.5. Both gellan hydrogels and PEGDA hydrogels demonstrate ability to rapidly adjust pH in deionized water and maintain pH regulation over several days in phosphate-buffered saline.
Figure 3B:
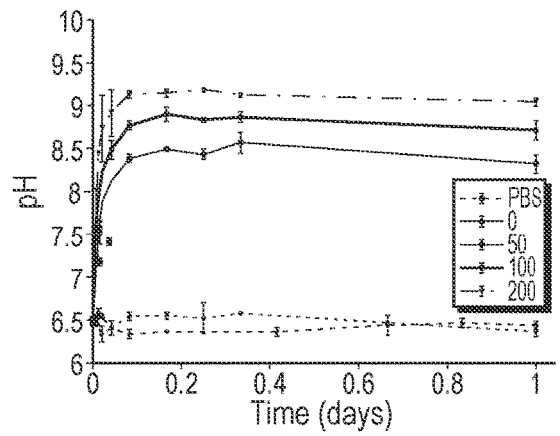
Figure 3C:
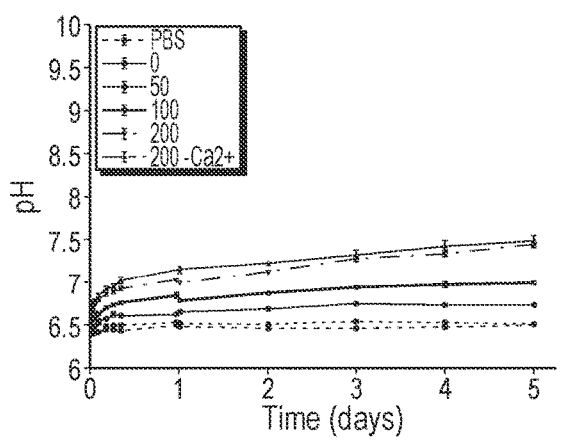
Figure 3D:
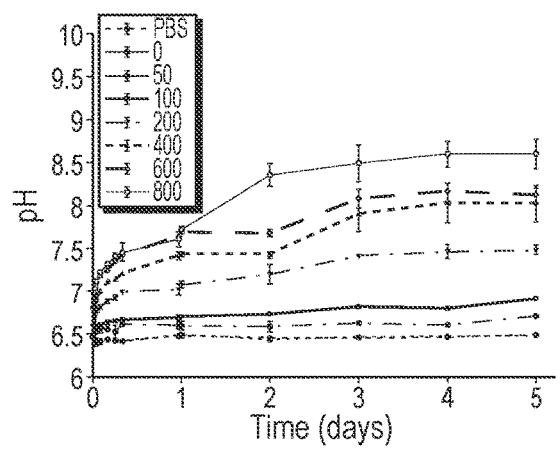

To better understand long-term bicarbonate release, pH profiles of solutions containing gellan and PEGDA with different sodium bicarbonate concentrations were obtained in deionized water and phosphate-buffered saline solutions. Deionized water represents a non-buffered solution that is highly susceptible to pH fluctuation, while phosphate-buffered saline contains self-buffering capabilities. Both deionized water and phosphate-buffered saline solutions were adjusted to a pH of 6.5. The inventors chose pH 6.5 as a representative value for the acidic tumor microenvironment. See Swietach, Cancer and Metastasis Reviews, 38.12 (June 2019). The solutions without hydrogel and the solutions containing hydrogels without bicarbonate were used as control groups to eliminate any pH changes produced by the solution or the gels. $NaHCO_3$-loading of both Gellan and PEGDA formulations exhibited a rapid increase in pH within the first hour in both deionized water and phosphate-buffered saline regardless of loaded bicarbonate concentration. See FIGS. 3A-3D. This initial burst release of $NaHCO_3$ can be attributed to the initial swelling of the hydrogels in the solutions. After the initial burst release, in deionized water, the pH levels remained relatively constant over the next twenty-four hours. See FIG. 3A and FIG. 3B. In phosphate-buffered saline, after the rapid initial increase of pH after gel immersion, there was a gradual increase in pH until saturation. See FIG. 3C and FIG. 3D. The inherent phosphate-buffered saline buffering system of salts and phosphates causes a slower rate of pH change in phosphate-buffered saline compared to deionized water. PEGDA hydrogels reached saturation in phosphate-buffered saline for all $NaHCO_3$-loading concentrations within four days. See FIG. 3B and FIG. 3D. Gellan hydrogels, at the same $NaHCO_3$-loading concentrations, increased the pH at a rate slightly slower than PEGDA hydrogels. See FIG. 3A and FIG. 3C. These data show that the gellan and PEGDA hydrogels release bicarbonate buffer into their surrounding solution, leading to a rapid initial increase in the solution's pH. See FIGS. 3A-3D. These data show that the gellan and PEGDA hydrogels release bicarbonate buffer into their surrounding solution, leading to a rapid initial increase in the solution's pH. See FIGS. 3A-3D. Regulation of the pH may be adjusted to different pH values depending on the concentration of bicarbonate loaded in the hydrogel and solutions. See FIG. 3. These assays show that gellan and PEGDA hydrogels can be tuned by loading different amounts of buffer to regulate pH towards a range of desired values. The findings in FIGS. 2A-2B and FIGS. 3A-3D demonstrate the potential use of $NaHCO_3$-loaded gellan and PEGDA hydrogels for controlling cancer tumor environments by countering gradual acidification. However, to produce alkaline pH levels and sustained long-term buffering above 7.0, a high sodium bicarbonate loading capacity is required. A limitation of gellan is the inconsistent gelation associated with high bicarbonate loading. PEGDA hydrogels were used in the cancer cell assays to maintain high loading capacity.

Example 5

Elastic Modulus and Swelling Ratio

Gels can be fabricated with tunable mechanical properties suited for various tissue environments. The elastic moduli of PEGDA and gellan hydrogels were measured to evaluate the effect of the encapsulates on the mechanical properties of the hydrogels. The effect of mono- and divalent ions on the gelation of gellan hydrogels has been studied. In gellan, lower pH protonates the glucuronate carboxylic group that reduces repulsive forces between the helical structure, promoting aggregation and gel formation. See Picone & Cunha, Carbohydrate Polymers, 84.1 (2011); Horinaka, Kani, Hori, and Maeda. Biophysical Chemistry, 111.3 (2004). This repulsion can also be overcome by addition of cations that can screen the electrostatic repulsion. Xu, Li, Jiang, & Bratlie, ACS Omega, 3.6 (2018).

Figure 4A:
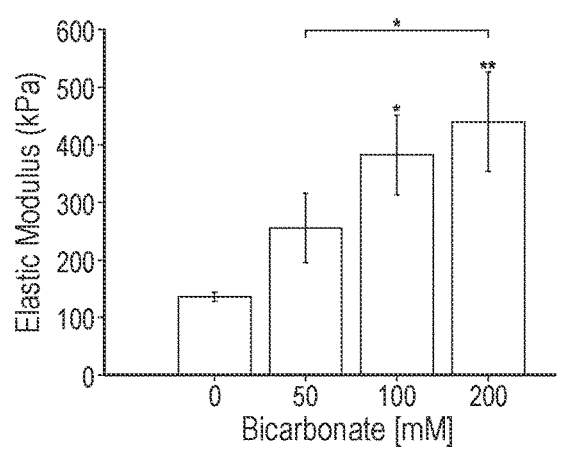
FIGS. 4A-4B are a pair of bar graphs showing the elastic modulus of gellan gels and PEGDA hydrogels relative to the loaded sodium bicarbonate concentration.
Figure 4B:
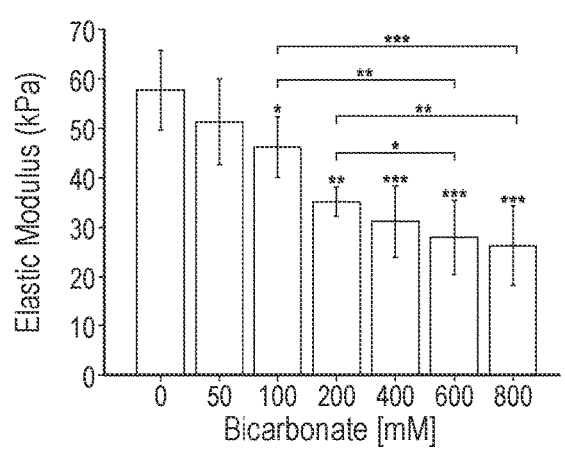
Figure 5A:
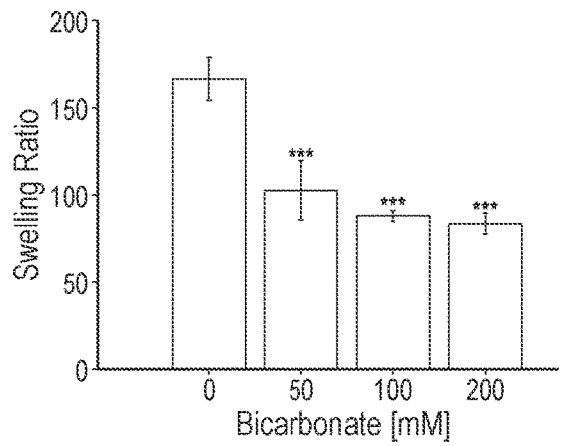
FIGS. 5A-5B are a pair of graphs showing the swelling of gellan and PEGDA hydrogels loaded with increasing sodium bicarbonate concentration.
Figure 5B:
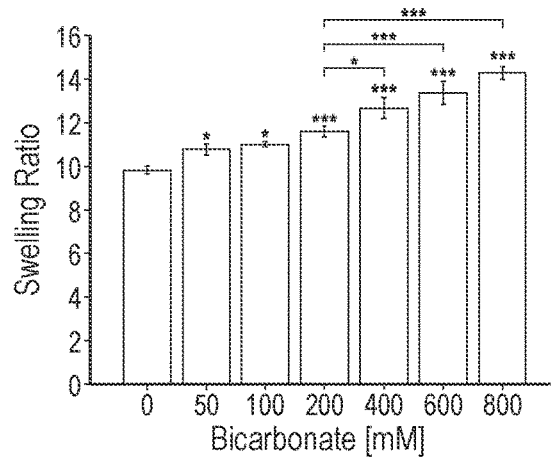
Figure 10:
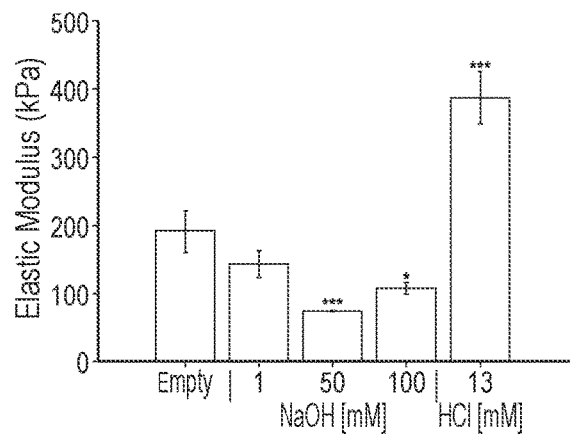
FIG. 10 is a graph showing the Elastic Modulus of gellan hydrogels depends on the encapsulated pH buffering solution. Loading of NaOH solution reduces the elastic modulus of the gellan hydrogel (compared to unloaded empty hydrogel). An increase of NaOH loading from 1.0 mM to 50 mM NaOH contributed to a lower gel stiffness. The stiffness then increased with further increased NaOH loading from 50 mM to 100 mM. Conversely, Hydrochloric acid loading (13 mM) of gellan hydrogels significantly increases the gel's elastic modulus. Each value represents the mean±standard deviation (n=3). *:p<0.05, **:p<0.001 compared with unloaded gellan hydrogel.
Figure 11:
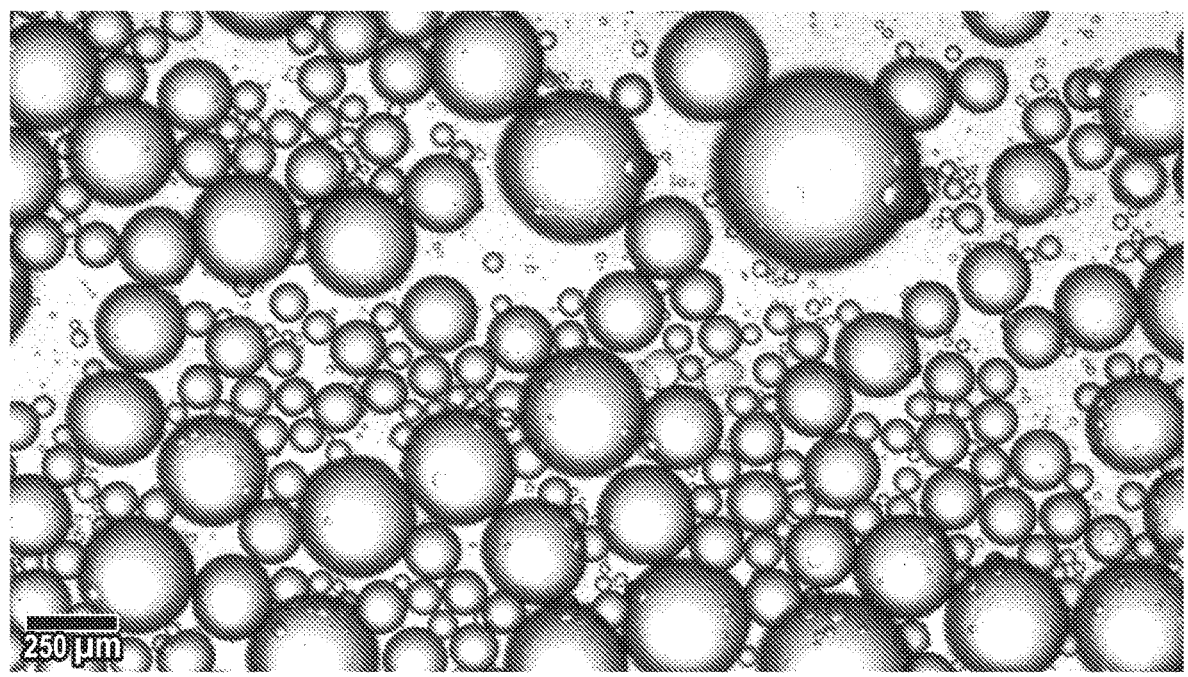
FIG. 11 is an image of PEGDA hydrogel formulations in microgel format created using surfactant-free suspension polymerization. Gels range in diameter from 1-500 uM.
Figure 12:
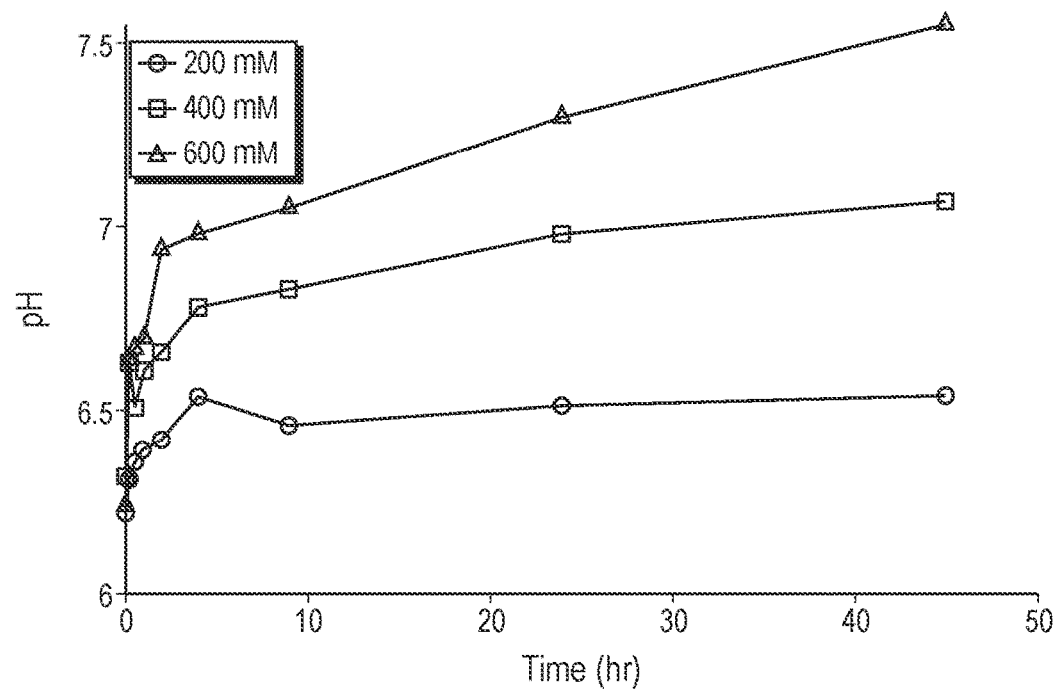
FIG. 12 is a graph showing the pH regulation profile of sodium bicarbonate loaded chitosan-PEGDA hydrogel formulations over time phosphate-buffered saline adjusted to acidic pH. Chitosan-PEGDA hydrogels demonstrate ability to rapidly adjust pH in phosphate-buffered saline over several days in phosphate-buffered saline. In phosphate-buffered saline, due to the inherent buffering molecules, pH equilibrates gradually over several days.

Gellan hydrogels loaded with sodium bicarbonate (0-200 mM) showed that increases in bicarbonate concentration in the polymer mixture contributed to a higher gel stiffness. For $NaHCO_3$-loaded gellan, the elastic moduli ranged between 136 kPa to 440 kPa for 0 to 200 mM bicarbonate. See FIG. 4A. Greater stiffness is expected to be caused by enhanced cross-linking from $Ca^{2+}$ and $Na^+$ ions and the less significant effect of $HCO_3^-$ molecule's weak electrostatic repulsion. Overall, gellan hydrogels with hydroxide were weaker due to the excessive repulsion between COO— groups on the polymer chains observed at a high pH, while the inverse held true for HCl-loaded gellan gels. See FIG. 10. Bicarbonate, being a weaker base, did not contribute highly to the electrostatic repulsion, and the $Na^+$ concentration largely dominated variations in mechanical strength. For PEGDA hydrogels, the elastic modulus decreased with an increasing bicarbonate concentration, from 57 kPa to 26 kPa for 0 to 800 mM PEG-$NaHCO_3$. See FIG. 4B. Reactions between bicarbonate and dimethacrylate groups on the polymer chain ends causes a release of carbon dioxide that gives rise to enhanced porosity in the gel network structure. Kabiri, Omidian, & Zohuriaan-Mehr. Polymer International, 52.7 (2003). Enhanced gel porosity results in decreased gel stiffness. Lower molecular weight PEGDA and higher PEGDA concentrations can increase elastic modulus. Tuning of bicarbonate encapsulation provides a control mechanism for PEGDA gel stiffness and porosity to adjust gels for different tissue environments. Smart biotherapeutics can be developed for a variety of biomedical applications by combining elastic modulus and porosity control with pH regulating effects.

The inventors examined swelling properties by placing the gel samples in a PBS solution for seven days, followed by oven heating for twenty-four hours at 80° C. Gel masses were measured after each wetting and drying cycle to calculate swelling ratios. Gellan hydrogels were evaluated with 0 to 200 mM loaded sodium bicarbonate, and PEGDA hydrogels were evaluated with 0 to 800 mM loaded sodium bicarbonate.

Gellan hydrogels exhibited a loss of shape after drying in the oven, caused by loss of their water content. The swelling ratio and water retention decreased from 167 t 13.0 to 83.6±6.4 as the bicarbonate concentration increased from 0 to 200 mM. This reduction in swelling properties is likely induced by the formation of a stronger polymer network due to sodium bicarbonate. This was corroborated by the analysis of the mechanical strength of the gellan hydrogels by the formation of a stiffer network with increasing bicarbonate concentration. PEGDA hydrogels increased swelling ratio and water retention from 9.8 t 0.2 to 14.3±0.3 as bicarbonate concentration increased from 0 to 800 mM. This is due to the formation of a highly porous network structure which contributes to an increased swelling ratio. The swelling of PEGDA hydrogels was almost 10 times lower than that of gellan hydrogels, suggesting that PEGDA hydrogel's reduced swelling characteristics can prolong the release of encapsulated bicarbonate.

Example 6

In Vitro Demonstration of Increased Doxorubicin Efficacy with pH Regulation

Figure 6A:
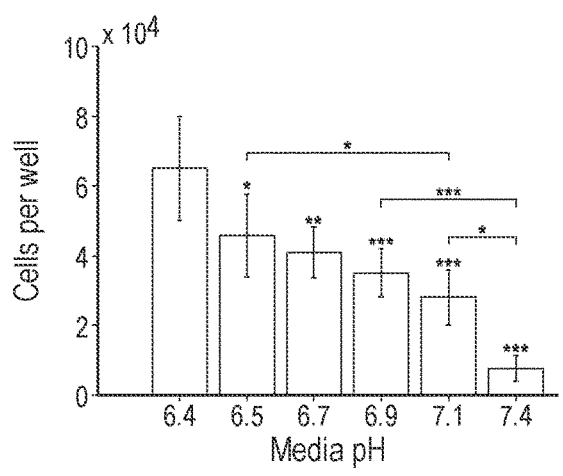
FIGS. 6A-6B are a pair of bar graphs showing pH-dependent chemotherapeutic efficacy using doxorubicin and MDA-MB-231 breast cancer cells.
Figure 6B:
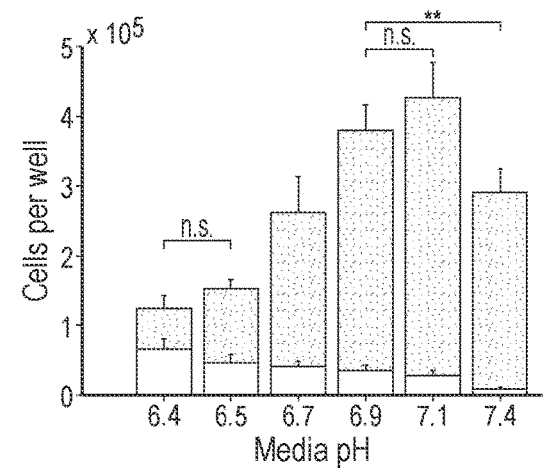

This EXAMPLE demonstrates a biological application of pH-regulating hydrogels, in which $NaHCO_3$-loaded PEGDA hydrogels regulate pH to reduce ion trapping. Ion trapping of weak base chemotherapeutics depends on the extracellular acidity in the tumor microenvironment. See FIG. 1. See also Raghunand, Mahoney, & Gillies, Biochemical Pharmacology, 66.7 (October 2003). The inventors demonstrated decreased doxorubicin efficacy at lower pH values (ion trapping) by exposing MDA-MB-231 breast cancer cells to 0.25 μM doxorubicin at various pHs, ranging from the acidic pH values (pH 6.4) of the tumor microenvironment to the neutral physiological pH (pH 7.4). The inventors prepared this range of pH media by adding varying amounts of free bicarbonate to bicarbonate-free DMEM. After a 5-day treatment duration, doxorubicin was more efficacious at preventing cell proliferation at pH 7.4 compared to acidic pHs. See FIG. 6A. Cell proliferation decreased at neutral pHs despite the cell's tendency towards greater proliferation in their adapted environment of neutral media. Pillai, Damaghi, Marunaka, Spugnini, Fais, & Gillies, Causes, consequences, and therapy of tumors acidosis (June 2019). When compared to cell cultures subjected to the same pH range but without doxorubicin treatment, the cell growth prevented by doxorubicin exposure increases rapidly from pH 6.5 to pH 6.8 and gradually increases towards pH 7.4. See FIG. 6B. At physiologically neutral values (pH 7.4), doxorubicin is approximately 95% effective at preventing cell proliferation compared to 40% efficacy at acidic values (pH 6.5). These results confirm that neutralization of the tumor microenvironment through bicarbonate media buffering increase chemotherapeutic efficacy.

Figure 7A:
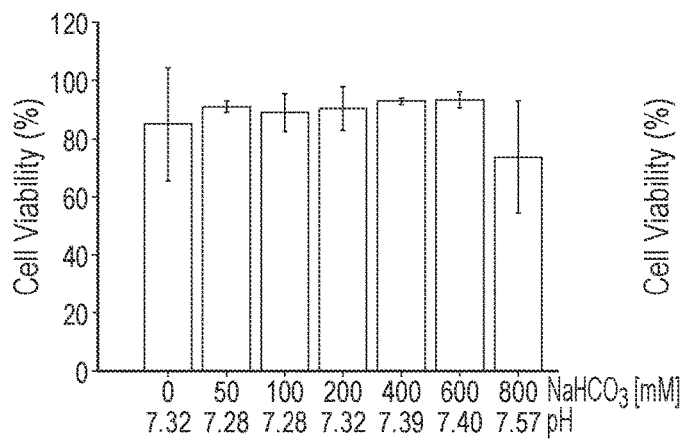
FIGS. 7A-7B are a pair of bar graphs showing the toxicity of PEGDA hydrogels was quantified using MTT viability assay after five days of treatment by bicarbonate-loaded PEGDA hydrogels.
Figure 7B:
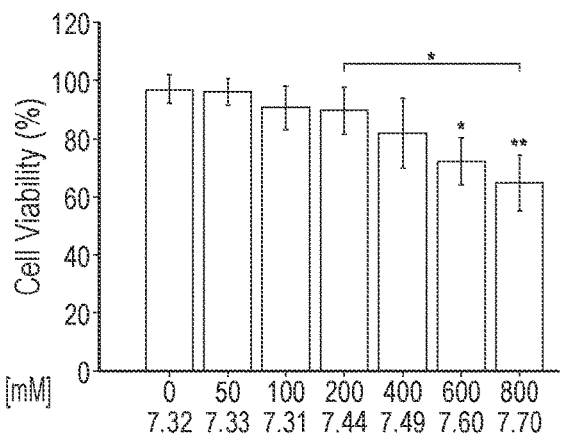

To validate the base eluting PEGDA hydrogels as a potential pH regulation mechanism to prevent ion trapping. The inventors first confirmed that the PEG-based hydrogels are non-toxic to cell cultures. The inventors exposed MCF-10A breast cells and MDA-MB-231 breast cancer cells to sodium bicarbonate-loaded PEGDA hydrogels to assess potential cytotoxicity. The inventors placed PEGDA gels loaded with 50 mM, 100 mM, 200 mM, 400 mM, 600 mM, and 800 mM bicarbonate in MEGM media of MCF-10A cell monolayers. See FIG. 7A. Percentage cell viability was calculated using an MTT (cell metabolic activity) assay. Similar gel formulations were applied to DMEM media of MDA-MB-231 cell monolayers. See FIG. 7B. Both assays used negative controls (no PEGDA gels) and vehicle controls (unloaded PEGDA gels). PEGDA gels were nontoxic to both cell lines based on no significant differences in cell viability in trials of low bicarbonate loading. Greater than 80% cell viability persisted up to 600 mM loaded bicarbonate in MCF-10A cell trials and up to 400 mM loaded bicarbonate in MDA-MB-231 cell trials. Compare FIG. 7A with FIG. 7B. Higher bicarbonate loading concentrations (800 mM for MCF-10A; 600 mM and 800 mM for MDA-MB-231) induced a change in media pH to above 7.4, at which point cell viability declined. This reduced viability may be caused by excessive media alkalinity beyond physiological bounds of 7.4. See, Hopkins, Sanvictores, & Sharma, Urolithiasis (September 2021); Michl, Park, and Swietach, Communications Biology 2.1 (December 2019).

The inventors confirmed that the PEGDA hydrogel is non-toxic to both healthy and cancerous breast cell lines. The inventors then tested the hydrogel's ability to prevent ion trapping and increase chemotherapeutic efficacy in acidic environments. Adhered MDA-MB-231 cells were cultured in 12-well plates using DMEM at pH 6.7 to express the acidic conditions of the tumor microenvironment. Doxorubicin treatment (0.25 μM) was delivered in tandem with PEGDA hydrogels loaded with varying concentrations of sodium bicarbonate (0-800 mM). After 5 days of treatment, the inventors quantified an inverse relationship between cell viability and amount of loaded bicarbonate using MTT assay. The results showed doxorubicin delivery concurrent with higher bicarbonate loading of PEGDA hydrogels decreased cell viability compared to doxorubicin delivery without bicarbonate incorporation. Loading above 200 mM bicarbonate resulted in lowered cell viability—indicative of increased doxorubicin efficacy—and neutralization of media pH. See FIG. 8A. The relative difference between each bicarbonate loading condition, with or without doxorubicin, shows a gradually increasing efficacy of doxorubicin as media pH neutralizes from 6.8 to 7.4. See FIG. 8B. Confocal imaging was used to confirm a reduction in viable cells after pH neutralization by base-eluting hydrogels. These confocal images show cells with membrane (DiO, green) and nuclear (Hoechst, blue) stain after forty-eight hours of culture with doxorubicin. A reduced cell density can be seen in pH neutralized cultures. The relative difference between each bicarbonate loading condition +/−doxorubicin shows a gradually increasing efficacy of doxorubicin as media pH neutralizes from 6.8 to 7.4. See FIGS. 8A-8B. These findings demonstrate a use for bicarbonate-loaded PEGDA hydrogels as an adjuvant therapy to doxorubicin. A similar phenomenon holds true for co-delivery of bicarbonate and alternative weak base chemotherapeutics, including but not limited to mitoxantrone, sunitinib, paclitaxel, and daunorubicin.

Other Embodiments

Specific compositions and methods of hydrogels to regulate pH, neutralize tumor acidosis, and increase chemotherapeutic efficacy. The scope of the invention should be defined solely by the claims. A person having ordinary skill in the biomedical art will interpret all claim terms in the broadest possible manner consistent with the context and the spirit of the disclosure. The detailed description in this specification is illustrative and not restrictive or exhaustive. This invention is not limited to the particular methodology, protocols, and reagents described in this specification and can vary in practice. When the specification or claims recite ordered steps or functions, alternative embodiments might perform their functions in a different order or substantially concurrently. Other equivalents and modifications besides those already described are possible without departing from the inventive concepts described in this specification, as persons having ordinary skill in the biomedical art recognize.

All patents and publications cited throughout this specification are incorporated by reference to disclose and describe the materials and methods used with the technologies described in this specification. The patents and publications are provided solely for their disclosure before the filing date of this specification. All statements about the patents and publications' disclosures and publication dates are from the inventors' information and belief. The inventors make no admission about the correctness of the contents or dates of these documents. Should there be a discrepancy between a date provided in this specification and the actual publication date, then the actual publication date shall control. The inventors may antedate such disclosure because of prior invention or another reason. Should there be a discrepancy between the scientific or technical teaching of a previous patent or publication and this specification, then the teaching of this specification and these claims shall control.

When the specification provides a range of values, each intervening value between the upper and lower limit of that range is within the range of values unless the context dictates otherwise.

CITATION LIST

A person having ordinary skill in the biomedical art can use these patents, patent applications, and scientific references as guidance to predictable results when making and using the invention.

Patent Literature

WO 2013/050962 (Mitra Biotech Private Ltd) "ECM composition, tumor microenvironment platform and methods thereof" published 2013 Apr. 11.

WO 2015/061372 (Hemoshear, LLC) "in vitro model for a tumor microenvironment" published 2015 Apr. 30. Methods for mimicking a tumor microenvironment in vitro are provided. The methods comprise indirectly applying a shear stress upon at least one tumor cell type plated on a surface within a cell culture container. Methods for mimicking tumor metastasis and methods for testing drugs or compounds in such systems are also provided.

WO 2020/076805 (Crapaud Bio. Inc.)

WO 2020/131513 (Taproot Medical Technologies, LLC)

WO 2012/033953 (Halozyme, Inc.) Methods for assessing and identifying or evolving conditionally active therapeutic proteins Non-Patent Literature Abumanhal-Masanveh et al., Sodium bicarbonate nanoparticles modulate the tumor pH and enhance the cellular uptake of doxorubicin. Journal of Controlled Release, 296, pp. 1-13 (April 2018) (2019).

Alfarouk, Muddathir, & Shayoub, Tumor acidity as evolutionary spite. Cancers (Basel), 3(1), 408-414 (Jan. 20, 2011).

Aoi & Marunaka, Importance of pH homeostasis in metabolic health and diseases: crucial role of membrane proton transport. BioMed Re-Search International (2014), p. 598986 (2014).

Asgharzadeh, Molecular machineries of pH dysregulation in tumor microenvironment: Potential targets for cancer therapy. BioImpacts: BI, 7(2), 115 (2017).

Banerjee & Bose, Comparative effects of controlled release of sodium bicarbonate and doxorubicin on osteoblast and osteosarcoma cell viability. Materials Today Chemistry, 12 (June 2019), pp. 200-208.

Brahimi-Horn et al., Hypoxia signalling controls metabolic demand. Current Opinion in Cell Biology, 19(2), 223-229 (April 2007)

Brahimi-Horn et al., Hypoxia and cancer. J. Mol. Med. 85(12), 1301-1307 (December 2007).

Cappuyns & Swennen, The application of pHstat leaching tests to assess the pH-dependent release of trace metals from soils, sediments and waste materials. Journal of Hazardous Materials 158.1 (October 2008), pp. 185-195.

Cardone et al., Nature Reviews Cancer 5, p. 795 (2005)

Chavez, Garimella, & Lipkowitz, Triple negative breast cancer cell lines: One tool in the search for better treatment of triple negative breast cancer. Breast Disease, 32(1-2), 35-48 (Dec. 30, 2010).

Chen, Howison, Jeffery, Robey, Kuo, & Pagel, Evaluations of extracellular pH within in vivo tumors using acido-CEST MRI. Magnetic Resonance in Medicine, 72(5). 1408-1417 (Nov. 26, 2015).

Chiche et al., Tumour hypoxia induces a metabolic shift causing acidosis: A common feature in cancer, J. Cell. Mol. Med., 14 (4), 771-794 (April 2010)

Cohen, Woods, & Krebs, Clinical and biochemical aspects of lactic acidosis, Vol. 162. (Oxford; Blackwell Scientific Publications; 1976).

Damaghi, Wojtkowiak, & Gillies, pH sensing and regulation in cancer. Frontiers in Physiology, 4, 370 2013 (Oct. 18, 2013).

DeSantis et al. Breast cancer statistics, 2019. CA: A Cancer Journal for Clinicians, 69(6), 438-451 (Oct. 2, 2019).

Devanaboyina et al., The effect of pH dependence of antibody-antigen interactions on subcellular trafficking dynamics, mAbs, 5(6), 851-859 (Sep. 5, 2013).

Diaz-Ruiz, Rigoulet, & Devin, The Warburg and Crabtree effects: On the origin of cancer cell energy metabolism and of yeast glucose repression. Biochimica et Biophysica Acta (EBA)—Bioenergetics, 1807(6), 568-576 (June 2011).

Ellis & Morrison, Buffers of constant ionic strength for studying pH-dependent processes. Methods in Enzymology 87.C (January 1982). pp. 405-426.

Estrella et al., Acidity generated by the tumor microenvironment drives local invasion. Cancer Research, 73(5), 1524-1535 (Jan. 3, 2013).

Fadaka et., Biology of glucose metabolization in cancer cells. Journal of Oncological Sciences, 3.2 (July 2017). pp. 45-51.

Faes et al., Acidic pH reduces VEGF-mediated endothelial cell responses by downregulation of VEGFR-2; Relevance for anti-angiogenic therapies. Oncotarget, 7(52), 86026-86038 (Dec. 27, 2016).

Faes et al., Acidic tumor microenvironment abrogates the efficacy of mTORC1 inhibitors. Molecular Cancer, 15, 78 (Dec. 5, 2016).

Feng et al., The acidic tumor microenvironment: A target for smart cancer nanotheranostics (March 2018).

Feron, Pyruvate into lactate and back: From the Warburg effect to symbiotic energy fuel exchange in cancer cells. Radiotherapy and Oncology, 92(3), 329-333 (September 2009).

Gatenby & Gillies, A microenvironmental model of carcinogenesis. Nature Reviews Cancer, 8, 56-61 (2008)

Gerweck et al., The pH partition theory predicts the accumulation and toxicity of doxorubicin in normal and low-pH-adapted cells. British Journal of Cancer, 7(5-6), 838-842 (February 1999).

Gillies et al., Targeting acidity in cancer and diabetes. Biochimica et Biophysica Acta (EBA)—Reviews on Cancer, 1871(2), 273-280. (April 2019).

Gillies, Pilot, & Mahipal, Buffer therapy→buffer diet. Journal of Nutrition & Food Sciences, 8.2 (2018).

Goldman & Weigeri, Corrosive substance ingestion: A review. American Journal of Gastroenterology (Springer Nature). 79(2) (1984).

Grada et al., Research Techniques Made Simple: Analysis of Collective Cell Migration Using the Wound Healing Assay. Journal of Investigative Dermatology, 137(2), e11-e16 (February 2017).

Guy et al., Evaluation of the cell invasion and migration process: A comparison of the video microscope-based scratch wound assay and the Boyden chamber assay. Journal of Visualized Experiments, (129), 56337 (Nov. 17, 2017).

Hanahan, & Weinberg, Hallmarks of cancer: The next generation. Cell, 144 (5). 646-674 (Mar. 4, 2011).

Hao, Xu, & Li (2018). Manipulating extracellular tumour pH: An effective target for cancer therapy. RSC Advances, 8(39), 22182-22192.

Hashim et al., Reduction of metastasis using a non-volatile buffer. Clinical & Experimental Metastasis, 28(8), 841-849 (December 2011).

Hoang Thi, Pilkington, Nguyen, Lee, Park, & Truong, The importance of poly(ethylene glycol) alternatives for overcoming PEG Immunogenicity in drug delivery and bioconjugation. Polymers (Basel), 12(2), 298 (Feb. 2, 2020).

Hoemann et al., Chitosan rate of uptake in HEK293 cells is influenced by soluble versus microparticle state and enhanced by serum-induced cell metabolism and lactate-based media acidification. Molecules, 18(1), 1015-1035 (Jan. 15, 2013).

Hoffman, Hydrogels for biomedical applications. Advanced Drug Delivery Reviews, 64, 18-23 (2012).

Hopkins, Sanvictores, & Sharma, Physiology, acid base balance. Urolithiasis (September 2021), pp. 19-22.

Huber et al., Cancer acidity: An ultimate frontier of tumor immune escape and a novel target of immunomodulation. Seminars in Cancer Biology, 43, 74-89 (April 2017).

Huber et al., J. Transl. Med., 8, article no. 57 (Jun. 15, 2010)

Huber, Cancer acidity: An ultimate frontier of tumor immune escape and a novel target of immunomodulation. Seminars in Cancer Biology (2017), p. 16.

Ibrahim-Hashim & Estrella, Acidosis and cancer: From mechanism to neutralization. Cancer Metastasis Review, 38(1-2), 149-155 (Jun. 1, 2020).

Ibrahim-Hashim et al., Systemic buffers inhibit carcinogenesis in TRAMP mice. Journal of Urology, 188(2), 624-631 (Aug. 1, 2012).

Ibrahim-Hashim, Abrahams, Enriquez-Navas, Luddy, Gatenby, & Gillies, Tris-base buffer: a promising new inhibitor for cancer progression and metastasis. Cancer Medicine, 6(7), 1720-1729 (Jul. 7, 2017).

Ibrahim-Hashim et al., Free Base lysine increases survival and reduces metastasis in prostate cancer model. Journal of Cancer Science and Therapy, 1(4) (Nov. 19, 2013).

Jabbari, Sarvestmi, Daneshian, & Moeinzadeh, Optimum 3D matrix stiff. ness for maintenance of cancer stem cells is dependent on tissue origin of cancer cells. PloS one, 10(7), e0132377 (2015).

Jonkman, Cathcart, Xu, Bartolini, Amon, Stevens, & Colarusso, An introduction to the wound healing assay using live-cell microscopy. Cell Adhesion & Migration, 8 (5), 440-451 (Oct. 31, 2014).

Jung et al., Targeting CXCR4-dependent immunosuppressive Ly6Clow monocytes improves antiangiogenic therapy in colorectal cancer. Proceedings of the National Academy of Sciences of the United States of America, 114(39), 10455-10460 (Sep. 12, 2017).

Kane, Lactate oxidation at the mitochondria: a lactate-malate-aspartate shuttle at work. Frontiers in Neuroscience, 8, 366 (Nov. 25, 2014).

Keskar, Marion, Mao, & Gemeinhart, In vitro evaluation of macroporous hydrogels to facilitate stem cell infiltration, growth, and mineralization. Tissue Engineering Part A, 15(T), 1695-1707 (2009).

Kim et al., Implication of global environmental changes on chemical toxicity-effect of water temperature, pH, and ultraviolet B irradiation on acute toxicity of several pharmaceuticals in *Daphnia magna*. Ecotoxicology 19.4 (April 2010), pp. 662-669.

Konermann, Addressing a common misconception: Ammonium acetate as neutral pH "buffer" for native electrospray mass spectrometry. Journal of The American Society for Mass Spectrometry 28.9 (September 2017), pp. 1827-1835.

Krieg, Taghavi, Amidon, & Amidon, In vivo predictive dissolution: Transport analysis of the $CO_2$-bicarbonate in vivo buffer system. Journal of Pharmaceutical Sciences, 103.11 (November 2014), pp. 3473-3490.

Li & Mooney, Designing hydrogels for controlled drug delivery. Nature Reviews Materials, 1 (12), 1-17 (2016).

Li et al., Acidic pHe regulates cytoskeletal dynamics through conformational integrin β1 activation and promotes membrane protrusion. Biochimica et Biophysica Acta (BBA)-Molecular Basis of Disease, 1864.7 (July 2018), pp. 2395-2408.

Liang et al., pH-responsive injectable hydrogels with mucosal adhesiveness based on chitosan-grafted-dihydrocaffeic acid and oxidized pullulan for localized drug delivery. Journal of Colloid and Interface Science, 536, 224-234 (2019).

Liberti & Locasale, The Warburg effect: How does it benefit cancer cells? Trends in Biochemical Sciences. 41.3 (March 2016), pp. 211-218.

Livingston et al., Evaluation of PEG-based hydrogel influence on estrogen receptor driven responses in MCF7 breast cancer cells. ACS Biomaterials Science & Engineering, 5(11), 6089-6098 (2019).

Lopez-Serra et al., A DERL3-associated defect in the degradation of SLC2AI mediates the Warburg effect. Nature Communications, 5, 3608 (Apr. 3, 2014).

Magalhaes et al., Cortactin phosphorylation regulates cell invasion through a pH-dependent pathway. Journal of Cell Biology, 195(5), 903-920 (Nov. 28, 2011).

Malana, Bukhari, & Zohra, Synthesis, swelling behavior, and network parameters of novel chemically crosslinked poly(acrylamide-co-methacrylate-co-acrylic acid) hydrogels. Designed Monomers and Polymers, 17(3), 266-274 (2014).

Marinello et al., Metformin prevention of doxorubicin resistance in MCF-7 and MDA-MB-231 involves oxidative stress generation and modulation of cell adaptation genes. Scientific Reports, 9, 5864 (Apr. 10, 2019).

McCarty & Whitaker, Manipulating tumor acidification as a cancer treatment strategy. Altern. Med Rev, 15(3), 264-72 (2010).

Michl, Park, & Swietach, Evidence-based guidelines for controlling pH in mammalian live-cell culture systems. Communications Biology, 2, 144 (Apr. 26, 2019).

Michl, Park, and Swietach, Evidence-based guidelines for controlling pH in mammalian live-cell culture systems. Communications Biology, 2.1 (December 2019), p. 144.

Moiseenko, Effects of acidification on aquatic ecosystems. Russian Journal of Ecology 2005 36:2 36.2 (March 2005), pp. 93-102.

Moldan, Cosby, & Wright, Modeling past and future acidification of Swedish lakes. Ambio 42.5 (2013), pp. 577-586.

Murphy, & Courtneidge, The 'ins' and 'outs' of podosomes and invadopodia: characteristics, formation, and function. Nature Reviews Molecular Cell Biology. 12(7), 413-426 (Jun. 23, 2011).

Neina, The role of soil pH in plant nutrition and soil remediation. Applied and Environmental Soil Science 2019 (November 2019), pp. 1-9.

Palumbo, F. Federico, Pitarresi, G., Fiorica, & Giammona, G. (2020 Feb. 1). Gellan gum-based delivery systems of therapeutic agents and cells. Carbohydrate Polymers, 229, 115430.

Paradise, Lauffenburger, & van Vliet, Acidic extra-cellular pH promotes activation of integrin avb3. PLoS ONE, 6.1 (January 2011).

Parks, Cormerais, & Pouysségur, Hypoxia and cellular metabolism in tumour pathophysiology. The Journal of Physiology. 595(8), 2439-2450 (Feb. 19, 2017).

Persi et al., Systems analysis of intracellular pH vulnerabilities for cancer therapy. Nature Communications, 9(1), 1-11, 2997 (Jul. 31, 2018).

Pillai, Damaghi, Marunaka, Spugnini, Fais, & Gillies, Causes, Consequences, and Therapy of Tumors Acidosis. Cancer Metastasis Reviews, 38(1-2), 205-222 (Jun. 1, 2019).

Pilon-Thomas et al., Neutralization of tumor acidity improves anti-tumor responses to immunotherapies. Cancer Research, 76(6), 1381-1390 (Mar. 15, 2016).

Raghunand et al., Enhancement of chemotherapy by manipulation of tumour pH. British Journal of Cancer. 80(7), 1005-1011 (June 1999).

Raghunand, Mahoney, & Gillies. Tumor acidity, ion trapping and chemotherapeutics. Biochemical Pharmacology, 66.7, pp. 1219-1229 (October 2003).

Raghunand, Mahoney, van Sluis, Baggett, & Gillies, Acute Metabolic Alkalosis Enhances Response of C3H Mouse Mammary Tumors to the Weak Base Mitoxantrone. Neoplasia, 3(3), 227-235 (May 2001).

Razak et al., Cytotoxicity of eupatorin in MCF-7 and MDA-MB-231 human breast cancer cells via cell cycle arrest, anti-angiogenesis, and induction of apoptosis. Scientific Reports, 9, 1514 (Feb. 6, 2019).

Ribeiro et al., Buffer therapy for cancer. Journal of Nutrition & Food Sciences, 01.S2 (2012).

Riss et al., Cell viability assays. In: The Assay Guidance Manual. Bethesda, MD: Eli Lilly & Company and the National Center for Advancing Translational Sciences (2016).

Robey et al., Bicarbonate increases tumor pH and inhibits spontaneous metastases. Cancer Research, 69(6), pp. 2260-2268 (March 2009).

Rohani et al., Acidification of tumor at stromal boundaries drives transcriptome alterations associated with aggressive phenotypes. Cancer Research, 79(8), 1952-1966 (Apr. 15, 2020)

Sepantafar et al., Engineered hydrogels in cancer therapy and diagnosis. Trends in Biotechnology, 35(1), 1074-1087 (2017).

Shukla & Shukla, Tunable antibiotic delivery from gellan hydrogels. Journal of Materials Chemistry B, 6(0), pp. 6444-6458 (September 2018).

Shukla et al., Effect of polymer and ion concentration on mechanical and drug release behavior of gellan hydrogels using pictorial design. Journal of Polymer Science, 58(10), pp. 1365-1379 (May 2020).

Siegler, Midgley, Polman, & Lever. Effects of various sodium bicarbonate loading protocols on the time-dependent extracellular buffering profile. Journal of Strength and Conditioning Research, 24.9, pp. 2551-2557 (September 2010).

Silva, Yunes, Gillies, & Gatenby. The potential role of systemic buffers in reducing intratumoral extracellular pH and acid-mediated invasion. Cancer Research, 69.6, pp. 2677-2684 (March 2009).

Som et al., Monodispersed calcium carbonate nanoparticles modulate local pH and inhibit tumor growth in vivo. Nanoscale 8.25, pp. 12639-12647 (June 2016).

Spill, Reynolds, Kamm, & Zaman, Impact of the physical microenvironment on tumor progression and metastasis. Current Opinion in Biotechnology, 40, 41-48 (Aug. 1, 2016).

Stillman, Jarai, Raman, Patel. & Fromen, Degradation profiles of poly (ethylene glycol) diacrylate (PEGDA)-based hydrogel nanoparticles. Polymer Chemistry, 11(2), 568-580 (2020).

Sun, Chen, Cao, Liang, & Xu, Warburg effects in cancer and normal proliferating cells: Two tales of the same name. Genomics, Proteomics & Bioinformatics, 17(3), 273-286 (May 7, 2019).

Sung et al., Global cancer statistics 2020: GLOBOCAN estimates of incidence and mortality worldwide for 36 cancers in 185 countries. CA: A Cancer Journal for Clinicians, 1-41 (Feb. 4, 2021).

Swietach, Vaughan-Jones, Harris, & Hulikova, The chemistry, physiology, and pathology of pH in cancer. Philosophical Transactions of the Royal Society of London: Biological Sciences, 369(1638) (Mar. 19, 2014).

Swietach, What is pH regulation, and why do cancer cells need it? Cancer Metastasis Review, 38(1), 5-15 (Feb. 1, 2019).

Tabelin, Hashimoto, Igarashi, & Yoneda. Leaching of boron, arsenic, and selenium from sedimentary rocks: I1. pH dependence, speciation, and mechanisms of release. Science of The Total Environment 473-474 (March 2014), pp. 244-253.

Takahashi, Yamaguchi, & Yamaoka, A relatively small gradient of extracellular pH directs migration of MDA-MB-231 cells in vitro. International Journal of Molecular Sciences, 21(7), 2565 (Apr. 7, 2020).

Tavares-Valente et al., Disruption of pH dynamics suppresses proliferation and potentiates doxorubicin cytotoxicity in breast cancer cells. Pharmaceutics, 13.2 (February 2021), p. 242.

Trebinska-Stryjewska et al., Impact of medium pH on DOX toxicity toward HeLa and A498 cell lines. ACS Omega, 5.14 (April 2020), pp. 7979-7986.

Tsuchikama & An, Z. Antibody-drug conjugates: recent advances in conjugation and linker chemistries. Protein & Cell, 9(1), 33-46 (January 2018).

Vander Heiden, Cantley, & Thompson, Understanding the Warburg effect: The metabolic requirements of cell proliferation. Science, 324(5930), 1029-1033 (May 22, 2009).

Wali, Kunte, Koetsier, Bissonnette. & Roy, Polyethylene glycol mediated colorectal cancer chemoprevention: Roles of epidermal growth factor receptor and Snail. Molecular Cancer Therapeutics, 7(9), pp. 3103-3111 (Sep. 1, 2009).

Wang, Decker, Zechner, L., Krstin, & Wink, In vitro wound healing of tumor cells: inhibition of cell migration by selected cytotoxic alkaloids. BMC Pharmacology and Toxicology, 20(1), 4 (Jan. 9, 2019).

Whiteside, The tumor microenvironment and its role in promoting tumor growth. Oncogene, 27 (45), 5904-5912 (Oct. 6, 2013).

Wong, Ashton, & Dodou, Effect of crosslinking agent concentration on the properties of unmedicated hydrogels. Pharmaceutics, 7(3), 305-319 (2015).

Yang, Zhong, & Yuan, Does baking soda function as a magic bullet for patients with cancer? A mini review. Integrative Cancer Therapies, 19 (May 23, 2020).

Zalipsky & Harris, Introduction to chemistry and biological applications of poly(ethylene glycol) (1997).

Zhalnina et al., Soil pH determines microbial diversity and composition in the park grass experiment. Microbial Ecology 69.2 (February 2015), pp. 395-406.

Zhitomirsky & Assaraf, Lysosomal sequestration of hydrophobic weak base chemotherapeutics triggers lysosomal biogenesis and lysosome-dependent cancer multidrug resistance. Oncotarget, 6(2), 1143-56 (Jan. 20, 2015).

Textbooks and Technical References

Current Protocols in Immunology (CPI). Coligan et al., eds. (John Wiley and Sons, Inc., 2003).

Current Protocols in Molecular Biology (CPMB). Ausubel, ed. (John Wiley and Sons, 2014).

Current Protocols in Protein Science (CPPS), Coligan, ed. (John Wiley and Sons, Inc., 2005).

Janeway's Immunobiology 9th edition, Murphy et al., eds. (Taylor & Francis Limited, 2017).

Laboratory Methods in Enzymology: DNA. Lorsch, ed. (Elsevier, 2013).

Lewin's Genes XII. Krebs et al., eds. (Jones & Bartlett Publishers (2014).

Luttmann et al., Immunology (Elsevier, 2006).

Molecular Cloning: A Laboratory Manual, 4th edition. Green & Sambrook, eds. (Cold Spring Harbor Laboratory Press, Cold Spring Harbor, N.Y., USA, 2012).

Pharmaceutical Sciences 23$^{rd}$ edition (Elsevier, 2020).

The Encyclopedia of Molecular Cell Biology and Molecular Medicine, 2$^{nd}$ edition. Meyers, ed. (Wiley-Blackwell, 2004).

The Merck Manual of Diagnosis and Therapy. 19$^{th}$ edition (Merck Sharp & Dohme Corp., 2018).

Buffers—A Guide for the Preparation and Use of Buffers in Biological Systems (Calbiochem, 1997).

Perrin & Dempsey, Buffers for pH and Metal Ion Control (Springer Netherlands. April 1979).

All patents and publications cited throughout this specification are expressly incorporated by reference to disclose and describe the materials and methods that might be used with the technologies described in this specification. The publications discussed are provided solely for their disclosure before the filing date. They should not be construed as an admission that the inventors may not antedate such disclosure under prior invention or for any other reason. If there is an apparent discrepancy between a previous patent or publication and the description provided in this specification, the present specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date supplied by the publisher, the actual publication date shall control.

The invention claimed is:

1. An implant for improving an outcome of an anticancer therapy, chemotherapy or immunotherapy, the implant consisting of a soft material delivery vehicle that controls the pH of a surrounding tumor microenvironment solution, for use in actively controlling the pH of the solution to improve chemotherapeutic drug uptake and efficacy, hinder tumor growth, and inhibit metastasis after implantation of the implant in a tissue environment, the soft material delivery vehicle consisting of:

(a) a non-toxic, hydrophilic, cross-linked polymer soft material that can swell significantly when put into solution and retains a high water retention capability; wherein the soft material is selected from the group consisting of gellan, polyethylene glycol (PEG), chitosan, hyaluronic acid, alginate, agarose, polyvinyl alcohol, solubilized basement membrane matrix, fibrin, polyacrylamide, polyacrylic acid, cellulose, collagen, fibroin, silk, gelatin, peptide hydrogels, and any combination of these soft materials;

(b) an aqueous pH buffer solution encapsulated in the soft material that is released by diffusion out from the delivery vehicle to the surrounding solution that surrounds the implant after implantation; wherein the pH buffer solution is selected from the group consisting of imidazole, lysine, hydroxyl-methyl-amino-methane, Tris, lactic acid, sodium hydroxide, hydrochloric acid, sulfuric acid, calcium carbonate, calcium bicarbonate, bicarbonate, magnesium hydroxide, and a combination of these.

2. The implant of claim 1, wherein the soft material is operative to encapsulate a chemotherapeutic drug, whereby the drug and the pH buffer solution can be encapsulated for co-delivery.

3. The implant of claim 1, wherein the soft material includes a tunable mechanical property that is tuned to match a mechanical property of the tissue environment, the mechanical property comprising a Young's modulus, a stiffness, an elastic modulus, a compressive modulus, a storage modulus, a loss modulus, a shear modulus, or a combination thereof.

4. The implant of claim 1, wherein the soft material includes a swelling ratio ($Q_m$) calculated by the weight of the soft material after seven days of contacting the tumor microenvironment solution divided by the weight of the soft material before contacting the tumor microenvironment solution; and wherein the Qm is in the range from 9 to 175.

5. The implant of claim 1, wherein the implant is operative to be implanted with a tumor biopsy procedure and/or operative to be coupled to a tumor biopsy procedure.

6. A method of using the soft material delivery vehicle of claim 1, comprising the step of injecting the soft material directly into a tumor microenvironment before or after crosslinking using a syringe.

7. A method for treating a subject in need of a cancer treatment to reduce a cancer tumor growth and metastasis by alkalizing an extracellular tumor microenvironment at or near the cancer and by preventing an emergence of malignant phenotypes in the cancer, the method comprising the steps of:

(1) injecting the soft material delivery vehicle of claim 1 directly into a tumor microenvironment at or near the cancer before or after crosslinking using a syringe; and (2) monitoring one or more performances of the soft material delivery vehicle in the tumor microenvironment;

wherein said performances are including a drug release, a mechanical property, a swelling, a pH of the tumor microenvironment, or a cancer tumor growth.

* * * * *